(12) United States Patent
Igarashi

(10) Patent No.: US 11,234,580 B2
(45) Date of Patent: Feb. 1, 2022

(54) ENDOSCOPE ILLUMINATING OPTICAL SYSTEM

(71) Applicant: OLYMPUS CORPORATION, Hachioji (JP)

(72) Inventor: Tsutomu Igarashi, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 532 days.

(21) Appl. No.: 16/171,169

(22) Filed: Oct. 25, 2018

(65) Prior Publication Data

US 2019/0059701 A1  Feb. 28, 2019

Related U.S. Application Data

(63) Continuation of application No. PCT/JP2017/019028, filed on May 22, 2017.

(30) Foreign Application Priority Data

Jun. 17, 2016 (JP) .............................. JP2016-120712

(51) Int. Cl.
*A61B 1/00* (2006.01)
*A61B 1/07* (2006.01)
(Continued)

(52) U.S. Cl.
CPC ...... *A61B 1/00096* (2013.01); *A61B 1/00188* (2013.01); *A61B 1/0669* (2013.01);
(Continued)

(58) Field of Classification Search
CPC ......... A61B 1/00096; A61B 1/05; A61B 1/07; A61B 1/00188; A61B 1/0669;
(Continued)

(56) References Cited

U.S. PATENT DOCUMENTS

| | | |
|---|---|---|
| 2006/0052668 A1 | 3/2006 | Homma |
| 2011/0157574 A1 | 6/2011 | Kato et al. |
| 2016/0106306 A1 | 4/2016 | Furuta |
| 2016/0195706 A1 | 7/2016 | Fujii |

FOREIGN PATENT DOCUMENTS

| | | |
|---|---|---|
| JP | H10123435 A | 5/1998 |
| JP | 2006072098 A | 3/2006 |

(Continued)

OTHER PUBLICATIONS

International Preliminary Report on Patentability (IPRP) dated Dec. 18, 2018 (and English translation thereof) in counterpart International Application No. PCT/JP2017/019028.
(Continued)

*Primary Examiner* — Timothy J Neal
(74) *Attorney, Agent, or Firm* — Holtz, Holtz & Volek PC

(57) ABSTRACT

The endoscope illuminating optical system includes a transparent resin member, and a lighting member which outputs illumination light. The transparent resin member has a through hole in which an image sensor is disposed, a non-through hole in which the lighting member is disposed, an internal optical surface which is formed at an interior of the transparent resin member by the non-through hole, and an outer surface from which the illumination light incident on the transparent resin member via the internal optical surface, is emerged toward an object. The outer surface has a curved-surface area through which the illumination light passes, and the curved-surface area has a boundary with the through hole. In the curved-surface area, a displacement of each point of the curved-surface area from the boundary occurs in a direction away from the object.

5 Claims, 23 Drawing Sheets

(51) Int. Cl.
*A61B 1/307* (2006.01)
*G02B 23/24* (2006.01)
*G02B 13/04* (2006.01)
*A61B 1/06* (2006.01)

(52) U.S. Cl.
CPC .............. *A61B 1/0676* (2013.01); *A61B 1/07* (2013.01); *A61B 1/307* (2013.01); *G02B 13/04* (2013.01); *G02B 23/243* (2013.01); *G02B 23/2469* (2013.01)

(58) Field of Classification Search
CPC ....... A61B 1/0676; A61B 1/307; A61B 1/041; A61B 1/00163; A61B 1/002; A61B 1/055; G02B 23/243; G02B 23/2469; G02B 13/04
See application file for complete search history.

(56) References Cited

FOREIGN PATENT DOCUMENTS

| | | |
|---|---|---|
| JP | 2007325794 A | 12/2007 |
| JP | 2009207529 A | 9/2009 |
| JP | 2013188375 A | 9/2013 |
| JP | 2015036050 A | 2/2015 |
| WO | 2010113550 A1 | 10/2010 |
| WO | 2015005112 A1 | 1/2015 |
| WO | 2015015996 A1 | 2/2015 |

OTHER PUBLICATIONS

English-language translation of WO 2015/015996.
International Search Report (ISR) dated Aug. 15, 2017 issued in International Application No. PCT/JP2017/019028.
Written Opinion dated Aug. 15, 2017 issued in International Application No. PCT/JP2017/019028.
Chinese Office Action (and English language translation thereof) dated Jul. 3, 2020 issued in counterpart Chinese Application No. 201780026857.2.

ENDOSCOPE ILLUMINATING OPTICAL SYSTEM

CROSS-REFERENCE TO RELATED APPLICATION

The present application is a continuation application of PCT/JP2017/019028 filed on May 22, 2017 which is based upon and claims the benefit of priority from Japanese Patent Application No. 2016-120712 filed on Jun. 17, 2016; the entire contents of which are incorporated herein by reference.

BACKGROUND OF THE INVENTION

Field of the Invention

The present invention relates to an endoscope illuminating optical system.

Description of the Related Art

As an endoscope intended for internal organs of urinary system, an endoscope for urinary organs is available. In the endoscope for urinary organs, for making an insertion into the urethra easy, it is preferable that an outer diameter be not more than 7 mm. In such manner, the outer diameter of the endoscope for urinary organs is smaller than an outer diameter of an endoscope for alimentary tract which is widely known for medical examination of stomach and large intestine. Moreover, the internal organs of urinary system are normally filled with urine. Therefore, in an objective optical system to be used in the endoscope for urinary organs, an optical design envisaged for in-water observation is carried out.

For example, in International Unexamined Patent Application Publication No. 2015/015996, there is a description about in-water observation by endoscope. In a case of observing internal organs of urinary system by endoscope, a medium filling an observation space is a perfusion solution or urine of which water is the main constituent. In International Unexamined Patent Application Publication No. 2015/015996, it has been signified that it is reasonable to deem a refractive index of these media to be equivalent to the refractive index of water.

Moreover, in International Unexamined Patent Application Publication No. 2015/015996, it has been pointed out that a field of view at the time of in-water observation (hereinafter, referred to as 'in-water field of view') is narrowed with respect to a field of view at the time of observation in air (hereinafter, referred to as 'field of view in air'). In International Unexamined Patent Application Publication No. 2015/015996, a relationship of the field of view in air and the in-water field of view are shown as follows.

|  | Field of view in air | | | |
| --- | --- | --- | --- | --- |
|  | 180° | 160° | 140° | 120° |
| In-water field of view | 97.2° | 95.3° | 89.7° | 81.0° |

The field of view in air and in-water field of view are calculated by letting a refractive index in water for a d-line to be 1.333 and a lens nearest to an object in the endoscope objective optical system to be flat.

An endoscope for urinary bladder is one of the endoscopes for urinary organs. In the endoscope for urinary bladder, for exploring a pathological lesion throughout the interior of the urinary bladder, an operator carries out a combined operation of turning a front-tip of the endoscope, inserting and de-inserting an insertion portion, and returning the insertion portion of the endoscope. When the in-water field of view is wide, it is possible to reduce a frequency of these operations.

However, as described above, even in the endoscope optical system for urinary bladder with the field of view in air of 120°, the in-water field of view is narrowed to 81° at the time of practical use. When the in-water field of view is narrow, the frequency of operations to be carried out by the operator is to be increased. Consequently, it becomes difficult to carry out exploration of a pathological lesion efficiently throughout the interior of the urinary bladder.

For such reason, in an endoscope for carrying out in-water observation, widening of the in-water field of view has been desired. At the time of widening the in-water field of view, in an illuminating optical system, it is necessary to secure light distribution suitable for that in-water field of view.

In the endoscope for urinary bladder, it is indispensable to secure a channel for carrying out perfusion and treatment while maintaining a small outer diameter that enables the transurethral insertion. For this, in the endoscope for urinary bladder, it is indispensable that a structure having various functions can be mounted in a narrow front-end space of the endoscope. Furthermore, for improving the insertability, it is desirable that a shape of the front-end of the insertion portion is tapered.

As conventional endoscope illuminating optical systems, endoscope illuminating optical systems disclosed in International Unexamined Patent Application Publication No. 2015/015996, International Unexamined Patent Application Publication No. 2010/113550, Japanese Patent Application Laid-open Publication No. 2013-188375, Japanese Patent Application Laid-open Publication No. 2009-207529, Japanese Patent Application Laid-open Publication No. 2007-325794, and Japanese Patent Application Laid-open Publication No. 2006-072098, have been know. In these endoscope illuminating optical systems, either an optical design envisaged for in-water observation is carried out or the shape of the front end of the insertion portion is provided with a feature.

SUMMARY OF THE INVENTION

An endoscope illuminating optical system according to at least some embodiments of the present invention comprises, a transparent resin member, and a lighting member which outputs illumination light, wherein the transparent resin member has a through hole in which an image sensor is disposed, a non-through hole in which the lighting member is disposed, an internal optical surface which is formed at an interior of the transparent resin member by the non-through hole, and an outer surface from which the illumination light incident on the transparent resin member via the internal optical surface, is emerged toward an object, and the outer surface has a curved-surface area through which the illumination light passes, and the curved-surface area has a boundary with the through hole, and in the curved-surface area, a displacement of each point of the curved-surface area from the boundary occurs in a direction away from the object, and a shape of the curved-surface area in a cross section defined by a plane including a central axis of the through hole is a shape such that an angle of inclination at each point in the curved-surface area increases continuously and monotonously as drawn away from the central axis, and the following conditional expressions (1) and (2) are satisfied:

$$0.02 < Ziax/Ds < 0.08 \quad (1), \text{ and}$$

$$10° < Aiax < 35° \quad (2)$$

where,

Ziax denotes a distance when a distance up to a predetermined position was measured along the central axis with reference to the boundary, and here the predetermined position is a position at which an axis passes through a center of gravity of the internal optical surface and is parallel to the central axis intersects the curved-surface area, and regarding the sign, either positive or negative, of the distance, the distance is let to be positive when the boundary is positioned on an object side of the predetermined position, Ds denotes a maximum outer diameter of the transparent resin member, and Aiax denotes an angle of inclination at the predetermined position for the shape of the curved-surface area in the cross-section defined by the plane including the central axis and the predetermined position, and here the angle of inclination is an angle made by a tangent to a cross-sectional shape and an axis perpendicular to the central axis.

DETAILED DESCRIPTION OF THE INVENTION

An endoscope illuminating optical system according to an embodiment will be described below in detail by referring to the accompanying diagrams. However, the present invention is not restricted to the embodiments described below.

An endoscope illuminating optical system according to the present embodiment includes a transparent resin member and a lighting member which outputs illumination light, wherein the transparent resin member has a through hole in which an image pickup member is disposed, a non-through hole in which the lighting member is disposed, and an internal optical surface, and the internal optical surface is formed at an interior of the transparent resin member by the non-through hole, and the illumination light is incident on the transparent resin member via the internal optical surface, and is emerged toward an object from an outer surface of the transparent resin member, and the lighting member is a light guide or a light emitter, and the outer surface of the transparent resin member has a curved-surface area through which the illumination light passes, and the curved-surface area has a boundary with the through hole which is formed in the curved-surface area, and in the curved-surface area, a displacement of each point of the curved-surface area from the boundary occurs in a direction away from the object, and a shape of the curved-surface area in a cross section defined by a plane including a central axis of the through hole is a shape such that an angle of inclination at each point in the curved-surface area increases continuously and monotonously as drawn away from the central axis, and the following conditional expressions (1) and (2) are satisfied:

$$0.02 < Ziax/Ds < 0.08 \quad (1), \text{ and}$$

$$10° < Aiax < 35° \quad (2)$$

where,

Ziax denotes a distance when a distance up to a predetermined position was measured along the central axis with reference to the boundary, and here the predetermined position is a position at which an axis passes through a center of gravity of the internal optical surface and is parallel to the central axis intersects the curved-surface area, and regarding the sign, either positive or negative, of the distance, the distance is let to be positive when the boundary is positioned on an object side of the predetermined position, Ds denotes a maximum outer diameter of the transparent resin member, and Aiax denotes an angle of inclination at the predetermined position for the shape of the curved-surface area in the cross-section defined by the plane including the central axis and the predetermined position, and here the angle of inclination is an angle made by a tangent to a cross-sectional shape and an axis perpendicular to the central axis.

Figure 1A:
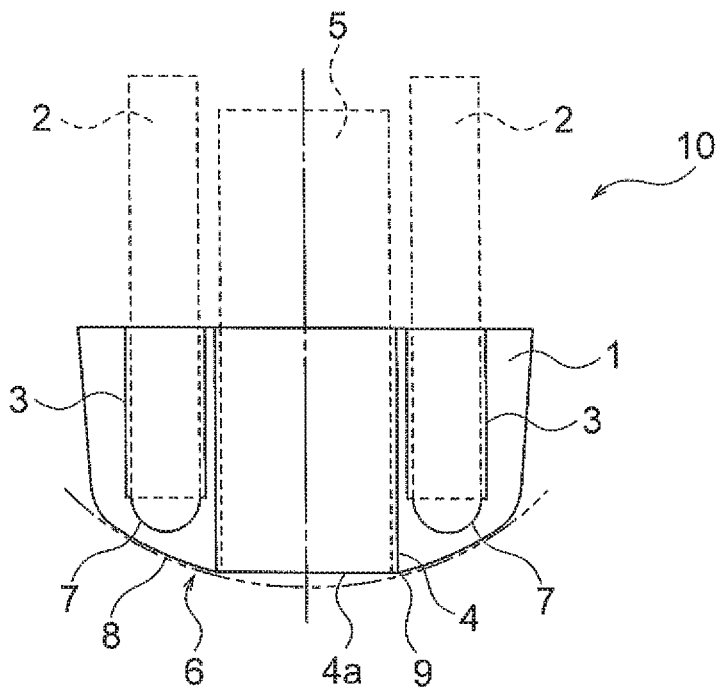
FIG. 1A, FIG. 1B, and FIG. 1C are schematic diagrams of an arrangement of an endoscope illuminating optical system according to the present embodiment.
Figures 1B, 1C:
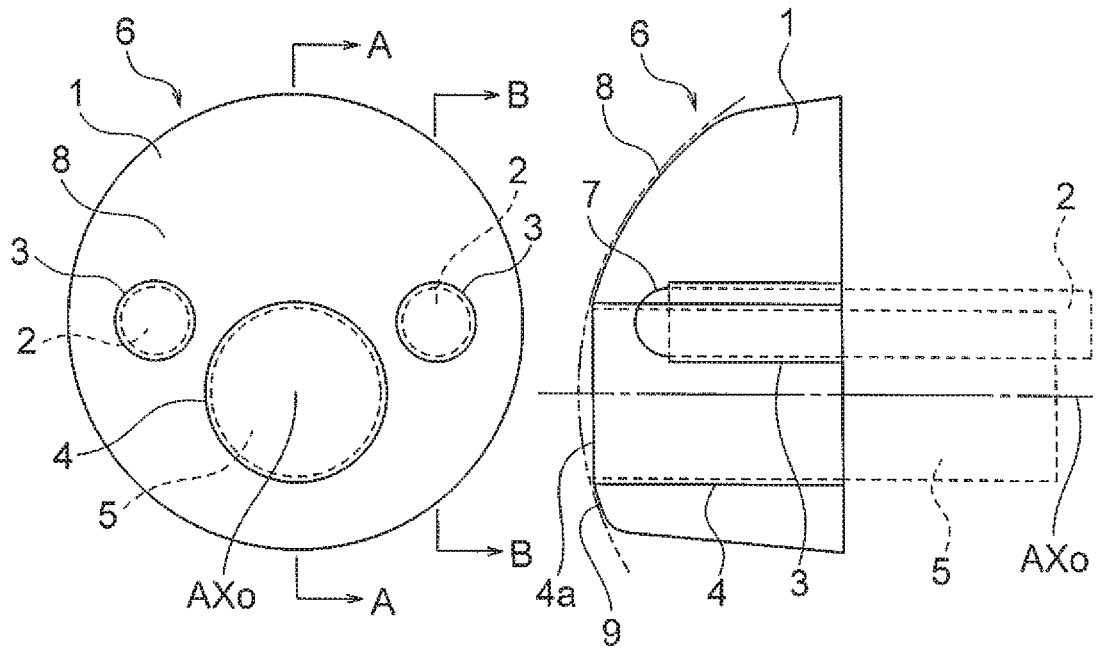

FIG. 1A, FIG. 1B, and FIG. 1C are schematic diagrams of an arrangement of the endoscope illuminating optical system according to the present embodiment. FIG. 1A is a top view, FIG. 1B is a front view, and FIG. 1C is a side view.

In FIG. 1A, a subject (an object) is positioned at a lower side of a transparent resin member 1, and in FIG. 1C, the subject (the object) is positioned at a left side of the transparent resin member 1. Therefore, in the following description, aside where the subject is positioned is let to be an 'object side', and a side where an image of the subject is positioned is let to be an 'image side'. Moreover, a space in which the subject is positioned is let to be an 'object space'.

Moreover, in the following description, upward-downward and leftward-rightward are used. Upward-downward signifies up and down of a paper surface, and leftward-rightward signifies left and right on the paper surface.

An endoscope illuminating optical system 10 includes the transparent resin member 1 and a lighting member 2. The endoscope illuminating optical system 10 is disposed at a front end of an insertion portion of an endoscope for example.

A non-through hole 3 and a through hole 4 are formed in the transparent resin member 1. The non-through hole 3 is a hole for disposing the lighting member 2. The through hole 4 is a hole for disposing an image pickup member 5.

In the non-through hole 3, the hole does not reach an outer surface 6 of the transparent resin member 1. An internal optical surface 7 is formed at an interior of the transparent resin member 1, at a position opposite to the lighting member 2. A shape of the internal optical surface 7 is concave toward the image side. Moreover, a curved-surface area 8 is positioned on the outer surface 6, at a position opposite to the internal optical surface 7.

Illumination light emerged from the lighting member 2 is incident on an interior of the transparent resin member 1 via the internal optical surface 7. The illumination light, upon being refracted or scattered by the internal optical surface 7, is emerged from the curved-surface area 8 to the object space, and illuminates the subject.

For example, a light guide is used for the lighting member 2. The light guide may be replaced by a light emitter such as a light emitting diode. Among light emitting diodes, there are light emitting diodes having light distribution characteristics close to perfect diffusion. In a case of using such light emitting diode, the shape of the internal optical surface 7 may be let to be convex toward the image side or flat, and not concave toward the image side. In such manner, in the internal optical surface 7, it is preferable to make an arrangement such that the light distribution characteristics are optimized by changing a shape of the surface in accordance with the light guide or the light emitter to be combined with the internal optical surface 7.

When the shape of the internal optical surface 7 is a shape that can be formed by modelling by a 3D-CAD (three-dimensional computer-aided design), it is possible to optical-design the internal optical surface. Therefore, the internal optical surface 7 is not restricted to a refracting surface or a surface defined by a single numerical expression. Moreover, it is not necessary to stick to whether it is axisymmetric or not axisymmetric.

For such reasons, the internal optical surface 7 may be a rough surface, a diffusing surface, or a surface having periodicity. A holographic diffusing surface is an example of the diffusing surface. Examples of the surface having periodicity are micro lens arrays and Fresnel surface.

Even when the internal optical surface 7 is a surface such as the abovementioned surfaces, there is no change in a desirable condition which the curved-surface area 8 has to satisfy. The desirable condition which the curved-surface area 8 has to satisfy will be described later.

Two non-through holes 3 and one through hole 4 are formed in the transparent resin member 1. The two non-through holes 3 are formed on a left side and a right side of the through hole 4 sandwiching the through hole 4. In this case, by the two lighting members 2, illumination light is irradiated from leftward-rightward direction on an image pickup area of the image pickup member 5.

In the endoscope illuminating optical system 10, two combinations of the internal optical surface 7 and the lighting member 2 are used. However, the number of combinations may be only one or more than two. Moreover, when there is a plurality of internal optical surfaces 7, it is preferable that the curved-surface area 8 positioned opposite to each internal optical surface 7 satisfy the desirable condition that will be described later.

The outer surface 6 has the curved-surface area 8. The illumination light passes through the curved-surface area 8 and is irradiated to the object. The through hole 4 is formed in the curved-surface area 8. An opening 4a of the through hole 4 is a flat surface. In such manner, a flat surface is included in the curved-surface area 8.

Characteristics of the shape of the overall curved-surface area 8 will be described below. The flat surface in the curved-surface area 8 is created by the through hole 4 being formed in the curved-surface area 8. The original shape of the overall curved-surface area 8, or in other words, the shape of the overall curved-surface area 8 before the through hole 4 being formed therein, is a curved surface which is convex toward the object side as shown by an alternate long and two short dashes line.

As mentioned above, in the curved-surface area 8, the opening 4a formed by the through hole 4. The curved-surface area 8 has a boundary 9 with the opening 4a. In the curved-surface area 8, a displacement of each point of the curved-surface area 8 from the boundary occurs in a direction moving away from the object. In other words, when a flat surface including the boundary 9 is let to be a reference surface, the displacement of each point of the curved-surface area 8 from the reference surface occurs toward the image side.

Figure 2A:
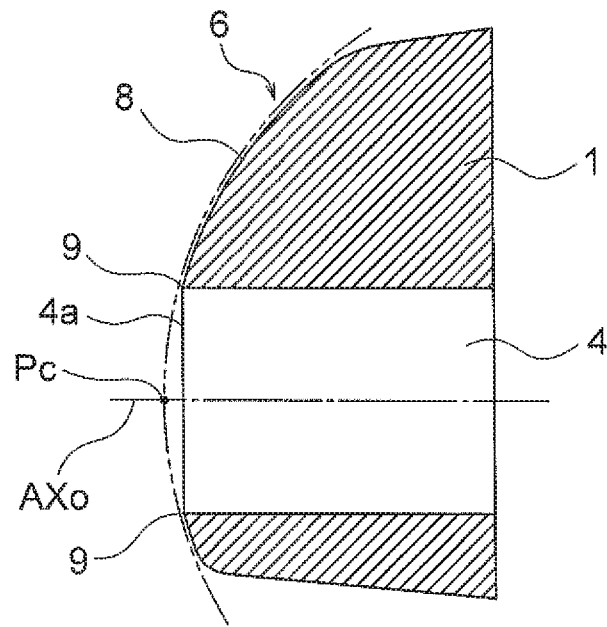
FIG. 2A and FIG. 2B are diagrams showing a cross-sectional shape of a transparent resin member.
Figure 2B:
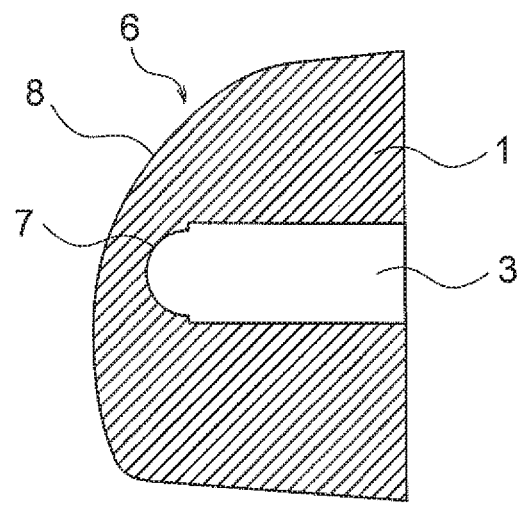

Characteristics of a cross-sectional shape of the curved-surface area 8 will be described below. FIG. 2A and FIG. 2B are diagrams showing a cross-sectional shape of the transparent resin member. FIG. 2A shows a cross-sectional shape between A-A in FIG. 1B, and FIG. 2B shows a cross-sectional shape between B-B in FIG. 1B.

There exists an infinite number of cross sections (hereinafter, referred to as 'predetermined cross sections') defined by a plane including a central axis AXo of the through hole 4. The cross-sectional shape shown in FIG. 2A is a shape of one of the infinite number of cross sections that exist.

It is possible to express the characteristics of a shape of the curved-surface area 8 by an angle of inclination. The angle of inclination is an angle made by a tangent to the cross-sectional shape and an axis perpendicular to the central axis AXo. The tangent to the cross-sectional shape is a tangent at an arbitrary point on a line expressing the cross-sectional shape of the curved-surface area 8.

The shape of the curved-surface area 8 in a predetermined cross-section is a curve shown by an alternate long and two short dashes line. As it is evident from the curve, in the shape of the curved-surface area 8 in the predetermined cross-section, an angle of inclination at each point in the curved-surface area 8 increases continuously and monotonously, as drawn away from the central axis AXo.

It is possible to express the characteristics of the shape of the curved-surface area 8 by a displacement. As mentioned above, in the overall curved-surface area 8, a displacement of each point of the curved-surface area 8 from the boundary 9 occurs in a direction moving away from the object. Therefore, even in the shape of the curved-surface area 8 in the predetermined cross section, a displacement of each point on the line expressing the cross-sectional shape from the boundary occurs in a direction moving away from the object. Moreover, an amount of displacement increases continuously and monotonously as the position of the point on the line expressing the cross-sectional shape draws away from the central axis AXo.

The cross-sectional shape shown in FIG. 2B is a shape of a cross-section not including the central axis AXo. Therefore, the cross-sectional shape shown in FIG. 2B is not a shape of the predetermined cross-section. However, in the overall curved-surface area 8, the displacement of each point of the curved-surface area 8 from the boundary occurs in a direction moving away from the object. As shown in FIG. 2B, even in a cross section other than the predetermined cross section, the angle of inclination at each point in the curved-surface area 8 increases continuously and monotonously as drawn away from the central axis AXo. Moreover, even the amount of displacement increases continuously and monotonously as the position on a point on the line expressing the cross-sectional shape draws away from the central axis AXo.

The transparent resin member 1 is provided to a front end of the insertion portion of the endoscope. Moreover, the image pickup member 5 is disposed in the through hole 4. Therefore, it is possible to describe the characteristics of the transparent resin member 1 by using the insertion portion and the image pickup member 5.

The boundary 9 is a boundary with the image pickup member 5 on the curved-surface area 8. Moreover, one end of the insertion portion is provided with the transparent resin member 1 and the other end thereof is provided with an operating portion.

The characteristics of the overall curved-surface area are as follows. The curved-surface area has a shape which is displaced toward the hand side of the insertion portion, directed from an area near the boundary with the image pickup member toward an outer periphery of the insertion portion.

The characteristics of the curved-surface area are as follows. With regard to a shape in a cross section defined by a plane through which the central axis of the image pickup member passes, at least in an orientation directed toward the internal optical surface from the central axis, the displacement and the angle of inclination increase continuously and monotonously with being directed toward the outer periphery from the central axis of the image pickup member.

The curved-surface area has a shape which is displaced toward the hand side of the insertion portion, directed from the area near the boundary with the image pickup member toward the outer periphery of the insertion portion, and a shape such that, in the orientation directed toward the internal optical surface from the central axis of the image pickup member, the displacement and the angle of inclination increase continuously and monotonously with being directed toward the outer periphery from the central axis of the image pickup member.

As shown in FIG. 1A and FIG. 1C, in an outer-diameter cross section viewed from the object-space side, the curved-surface area 8 not only covers the internal optical surfaces 7 adequately but also occupies an extremely wide range of the outer surface 6 side of the transparent resin member 1. Accordingly, it is possible to optical-design the entire surface of the curved-surface area 8 assuming as an optically effective range. Moreover, the curved-surface area 8 has a shape such that the displacement and the angle of inclination increase continuously and monotonously. Therefore, the discontinuity of refraction is hard to occur in that range, and it is possible to suppress an occurrence of uneven light distribution.

Since the curved-surface area 8 can be said to have a tapered shape which caused the image pickup member 5 to be protruded toward the object space, the curved-surface area 8 contributes to an improvement in the insertability as the endoscope. In a case of an endoscope for urinary bladder for instance, an insertion into the urethra improves. The shape of the curved-surface area 8 can contribute not only to an optical effect but also to realization of a smooth tapered shape with an object of improvement in the insertability.

The internal optical surface 7 has an effect of widening an angle distribution by diffusing light emerged from the lighting member 2. Therefore, the internal optical surface 7 virtually determines the light distribution characteristics of the overall illuminating system. For the internal optical surface 7, an optical refracting surface or a scattering surface of various shapes known heretofore may be used. In injection molding or mold manufacturing for injection molding, properties such as transferability and release ability become significant. When the properties such as transferability and release ability are taken into consideration, the internal optical surface 7 of refracting-surface type is desirable.

Moreover, in a case in which the refracting surface has a convex shape having a positive refractive power, various problems are susceptible to arise due to a focusing effect and an image forming effect at the refracting surface. The problems include thermal stability with respect to a living body, a thermal unfolding of resin at the time of mounting a transparent resin, and an occurrence of unevenness due to projection of mesh of an end surface of a light guide. Therefore, in the internal optical surface 7, a concave shape having a negative refractive power is to be used for a refracting surface. No matter what type of surface is the internal optical surface 7, for improving the refractive power and diffusivity, it is desirable that a refractive index of the transparent resin member 1 be high.

A shape in the outer peripheral area of the transparent resin member 1 or a shape in the area near the image pickup member 5 is determined by non-optical constraints. It is desirable that a position of the lighting member 2 and a position of the internal optical surface 7 be away from the shape determined by the non-optical constraints, in the outer-diameter cross section of the transparent resin member 1. Moreover, it is desirable that the position of the lighting member 2 and the position of the internal optical surface 7 maintain an appropriate distance from the image pickup member 5.

The curved-surface area 8 is retracted toward the hand side of the insertion portion as drawn away from the image pickup member 5. Consequently, when an attempt is made to secure a resin thickness at the position of the internal optical surface 7 with the same condition, the lighting member 2 and the internal optical surface 7 are also retracted toward the hand side of the insertion portion.

When the lighting member 2 and the internal optical surface 7 are retracted excessively toward the hand side of the insertion portion, a portion determined by the non-optical constraints such as light reaching the image pickup member or the area of the outer periphery increases. Moreover, when the lighting member 2 and the internal optical surface 7 come excessively close to the image pickup member 5, light directed toward the image pickup member 5 is shielded by the image pickup member 5. Therefore, it is desirable that in the outer-diameter cross section of the transparent resin member 1, the lighting member 2 and the internal optical surface 7 be positioned near the midpoint of an outer periphery and a boundary portion of the image pickup member 5 near the vertical center of the transparent resin member 1.

For the shape of the curved-surface area 8, it is not necessary to stick to an axisymmetric shape or a definition of the numerical expression in particular. It is preferable that the shape of the curved-surface area 8 be a shape that can be formed by 3D-CAD software modeling, and satisfies a desirable condition for the abovementioned curved-surface area 8.

By the curved-surface area being provided with such a characteristic shape, in the endoscope illuminating optical system according to the present embodiment, even in a case in which an angle of light distribution is wide, it is possible to suppress the uneven light distribution.

There are two factors that cause uneven light distribution. As a first factor, a fact that a portion of illumination light for which an angle of refraction of a light ray (hereinafter, referred to as 'angle of refraction') changes discontinuously is formed on an outer surface of the transparent resin member, may be cited. When the transparent resin member has such portion, the angle of refraction changes discontinuously in this portion.

Such portion is generated by a portion of an area through which the illumination light passes being provided with a distinct optically effective range. The optically effective range is provided at a position opposite to the light guide. The surface shape and direction of a normal of the surface differ substantially for the optically effective range and an area other than the optically effective range (hereinafter, referred to as 'ineffective range'). Consequently, the angle of refraction differs widely in the optically effective range and the ineffective range. As a result, the angle of refraction changes discontinuously at a border of the optically effective range and the ineffective range.

For illuminating an illumination range with a uniform brightness, it is preferable that light rays directed to the object at various angles be included in the illumination light. However, in a portion in which the angle of refraction changes discontinuously, light rays of a specific angle fall out or a large number of light rays of a specific angle are generated. As a result, a dark portion or a bright portion is developed in a portion of the illumination range, and the dark portion or the bright portion appears as uneven light distribution.

As mentioned above, the feature of the endoscope illuminating optical system according to the present embodiment is the shape of the curved-surface area 8. In the curved-surface area 8, the entire area has a smooth shape. In other words, no distinct optically effective area is formed at a position opposite to the internal optical surface 7 (lighting member 2) or in the vicinity thereof. Therefore, the curved-surface area 8 does not have a boundary of the optically effective range and the ineffective range. In other words, the portion in which the angle of refraction changes discontinuously does not exist in the curved-surface area 8. Consequently, even in the case in which the angle of light distribution is wide, it is possible to suppress uneven light distribution.

Moreover, the shape near the periphery of the transparent resin member 1 and the shape near the image pickup member 5 are shapes determined by the non-optical constraints. In a case of having such shape, an optical control such as a control of the angle of refraction is difficult. In the endoscope illuminating optical system according to the present embodiment, it is possible to extend the curved-surface area 8 up to a portion determined by the non-optical constraints. Therefore, it is possible to keep boundaries thereof at which it is difficult to secure the optical continuity at a distance from an axis of the non-through hole 3.

Illumination light emerged at a large angle from the lighting member 2 reaches a location away from the axis of the non-through hole 3 on the outer surface 6 side of the transparent resin member 1. The illumination light reached in this case is directed toward the illumination range. Here, in this case, not being included in the curved-surface area 8, refraction of the light ray is not optimized. Consequently, in this case, the light rays of a specific angle are susceptible to fall out or light rays of a specific angle are susceptible to be generated in large number.

However, light intensity of light rays reached this location is weak. Therefore, in the illumination light that has reached this location, even when the light rays of a specific angle are missing or light rays of a specific angle are generated in large number, an effect on normal illumination light, or in other words, illumination light that has passed through the curved-surface area 8, becomes small. In such manner, illumination light emerged at a large angle from the lighting member 2 hardly becomes a cause of the uneven light distribution. Therefore, according to the endoscope illuminating optical system according to the present embodiment, it is possible to suppress the cause of uneven light distribution.

The magnitude, large or small, of unevenness of light distribution has a trade-off relationship with the size, wide or narrow, of an angle of light distribution. The more the angle of light distribution is widened, the more a position at which the light emerged from the lighting member 2 passing through the outer surface 6 moves away from the axis of the non-through hole 3. Consequently, it is susceptible to have an effect of the boundary portion formed by the shape determined by the non-optical constraints. Therefore, at the time of realizing a wide-angle light distribution in water which is even wider than the light distribution in air, when no distinguishing idea such as the shape of the curved-surface area 8 has been devised in the illuminating optical system, it becomes difficult to achieve both of securing the wide angle of light distribution suitable for in-water observation and suppressing the uneven light distribution.

As a second factor, a fact that the angle of refraction is centered around a specific angle may be cited. This is because a portion at which the angle of refraction becomes constant is formed on an outer surface of the transparent resin member over a wide range. When the light rays of the specific angle increase, intensity of light at the specific angle becomes high. As the intensity becomes high, intensity of light at the other angle becomes relatively low. As a result, a dark portion or a bright portion is developed in a portion of the illumination range, and the dark portion or the bright portion appears as uneven light distribution.

In the endoscope illuminating optical system according to the present embodiment, in the curved-surface area 8, the angle of inclination is changed continuously. By doing so, it is possible to change the angle of refraction of light continuously. Consequently, the intensity of light at a specific angle does not become high. Therefore, it is possible to suppress the uneven light distribution.

A shape-definition formula of the curved-surface area 8 and the internal optical surface 7 will be described below. The shape of the curved-surface area 8 and the shape of the internal optical surface 7 may be an axisymmetric shape or a non-axisymmetric shape.

Moreover, a shape of an optical surface is a shape that can be modeled by 3D-CAD software, a design of an optical system in a practical optical design is possible. Therefore, for the shape-definition formula of the curved-surface area 8 and the internal optical surface 7, it is not necessary to stick to the definition formula that is expressed by a single numerical expression. For instance, the shape of the curved-surface area 8 and the shape of the internal optical surface 7 maybe defined my spline definition.

Here, to simplify the explanation, both the curved-surface area 8 and the internal optical surface 7 are let to have an axisymmetric surface shape, and the shape of the surface may be let to be defined by a single numerical expression. As an axisymmetric surface shape defined by a numerical expression, it may be any one of a spherical surface and an aspheric surface. In this case, a definition expression which is applicable to both the spherical surface and the aspheric surface is to be used. As local coordinates of a surface, when an optical axial direction is let to be Z-axis and an axis perpendicular to Z-axis is let to be S-axis, an axisymmetric aspheric surface definition formula in an S-Z cross section is shown in numerical expression (A).

$$Z'(S) = \frac{S^2/R}{1 + \sqrt{1-(1+K)*S^2/R^2}} \quad (A)$$

where,

S denotes a distance from the Z-axis

Z'(S) denotes a Z-coordinate obtained as a function of S,

R denotes a radius of curvature at a central portion of a spherical surface term in the S-Z cross section, and K denotes a coefficient which determines quadratic surface characteristics in the S-Z cross section.

In numerical expression (A), since Z'=0 when S=0, a point of intersection of the surface defined by the numerical expression and the Z-axis becomes a point of origin of Z'. It is possible to define the internal optical surface 7 only by this numerical expression.

For the curved-surface area 8, it is necessary to devise a method for getting the point of origin of the Z-axis. The curved-surface area 8 is a spherical surface having a center of curvature on a central axis AXo. No physical surface of the curved-surface area 8 exists at an inner side of the through hole 4. As shown in FIG. 2A, a point of intersection Pc of the Z-axis (central axis AXo) and the curved-surface area 8 (spherical surface) shown by an alternate long and two short dashes line is at a position protruded toward the object space of the opening 4a.

The point of intersection Pc indicates an object-side end of the curved-surface area 8. Moreover, a position of the opening 4a indicates a position of a front-end surface of the image pickup member 5. Hereinafter, the description will be made by using a front-end surface of the curved-surface area 8 and the front-end surface of the image pickup member 5.

As mentioned above, the object-side end of the curved-surface area 8 is positioned on the object-space side of the front-end surface of the image pickup member 5. Therefore, combining the front-end surface of the image pickup member 5 and the object-side end of the curved-surface area 8, the front-end surface of the image pickup member 5 is let to be a point of origin for a Z-coordinate of the curved-surface area 8. In the abovementioned conditional expression (1) or conditional expression (3) described later, Z-coordinate with the front-end surface of the image pickup member 5 as a base, is used. For the shift in the point of origin of Z-coordinate, Z' calculated by letting a radius of the image pickup member 5 in numerical expression (A) is to be subtracted.

It is possible to calculate the Z-coordinate with the front-end surface of the image pickup member 5 as a base by using numerical expression (B).

$$Z(S)=Z'(S)-Z'(\text{Sic}) \quad (B)$$

where,

Z(S) denotes a Z-coordinate with the front-end surface of the image pickup member as a base, obtained as a function of S, Sic denotes a radius of the front-end surface of the image pickup member, and Z'(Sic) is Z' at a radial position of the image pickup member.

In numerical expression (A), when K is let to be K=0, the curved-surface area 8 becomes a spherical surface. Moreover, when K is let to be K≠0, an aspheric surface of quadratic type can be defined as the surface of the curved-surface area 8. In such manner, numerical expression (A) can express both the spherical and aspheric surface.

In a normal aspheric surface definition expression, an even-order polynomial term is used. In numerical expression (A), to simplify the explanation, the even-order polynomial term is omitted. However, defining a shape including the even-order polynomial term poses no problem.

In a case of designing the curved-surface area 8 by using numerical expression (A), the tapered shape and the illumination optical characteristics are to be optimized by varying parameters R and K. Here, Z'(Sic) of numerical expression (B) which becomes a Z-axis offset value of the curved-surface area 8 changes with the variation in the value of R and the variation in the value of K. Therefore, Z'(Sic) is to be synchronized with the variation in the value of R and the variation in the value of K. The illumination optical characteristics are determined by a central illuminance and the light distribution characteristics, for instance. Therefore, by optimizing the illumination optical characteristics, it is possible to optimize the light distribution characteristics as well.

In a case in which the curved-surface area 8 is a spherical surface, the smaller the value of R, the stronger is the tapering tendency. Therefore, the insertability is improved. However, with the improvement in the insertability, the internal optical surface 7 also moves toward an image side. As the internal optical surface 7 moves toward the image side, the image pickup member 5 is susceptible to be exposed to the illumination light. In this case, since there is an adverse effect on the light distribution characteristics, it is necessary to balance the tapered shape and the illumination light characteristics by setting the value of R.

In a case in which the curved-surface area 8 is an aspheric surface, K is let to be K>0 (an elliptical shape with an S-axis direction as a long axis) with a large R. By doing so, it is possible to increase a displacement on an outer peripheral side of the curved-surface area 8 without moving the internal optical surface 7 much to the left side. Accordingly, it is possible to improve the degree of freedom of optimization of the tapered shape and the illumination optical characteristics.

In a case of designing the internal optical surface 7 according to numerical expression (A), the illumination optical characteristics are to be optimized by changing R and K. In a case in which the internal optical surface 7 is a spherical surface, the smaller the value of R, the more improved is the light distribution, but the central illuminance is degraded. Therefore, it is necessary to optimize the illumination optical characteristics, or in other words, to balance appropriately the light distribution characteristics and the central illuminance.

In a case in which the internal optical surface 7 is an aspheric surface, it is possible to control an illuminance distribution on the wide angle side by changing the value of K, with the central illuminance maintained as it has been. By letting the K to be K<0, a curvature in a peripheral portion of the internal optical surface 7 becomes small. As a result, it is possible to improve the illuminance distribution on the wide angle side.

In the endoscope illuminating optical system according to the present embodiment, the abovementioned conditional expressions (1) and (2) are satisfied.

Figure 3A:
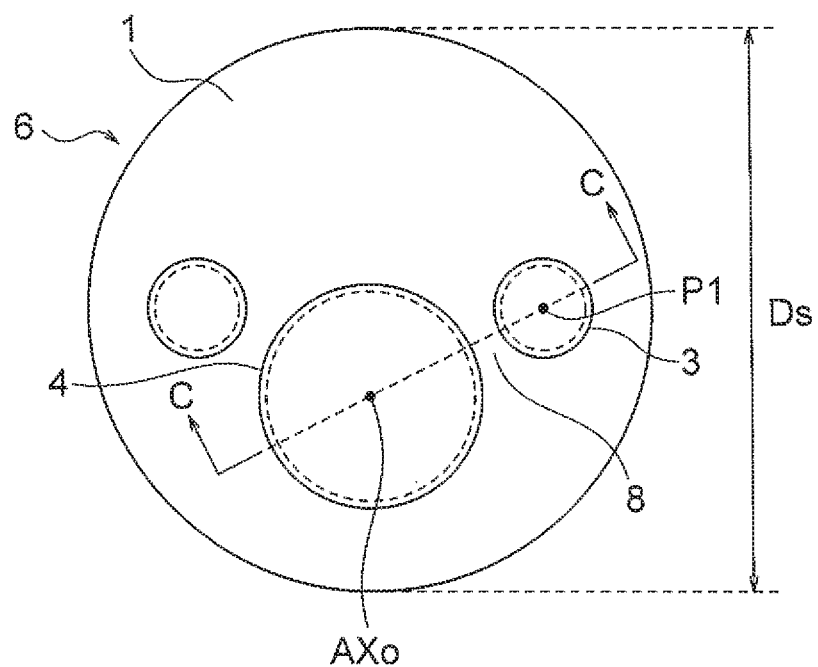
FIG. 3A and FIG. 3B are diagrams showing the transparent resin member.
Figure 3B:
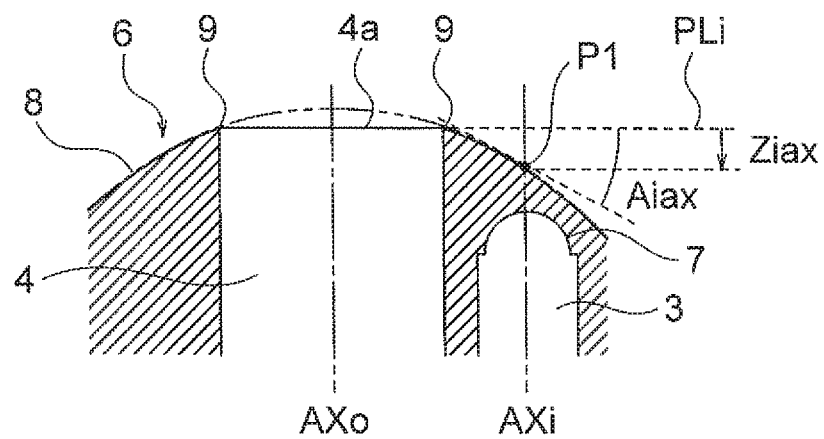

Here, Ziax and Ds in conditional expression (1) will be described below by using FIG. 3A and FIG. 3B. FIG. 3A and FIG. 3B are diagrams showing a transparent resin member. FIG. 3A is a front view and FIG. 3B is a diagram showing a cross-sectional shape between C-C in FIG. 3A.

The non-through hole 3 and the through hole 4 are formed in the transparent resin member 1. The opening 4a is formed in the curved-surface area 8 by the through hole 4. Accordingly, a boundary 9 with the opening 4a is formed in the curved-surface area 8.

Moreover, Ziax is distance when a distance up to a predetermined position was measured along the central axis AXo with reference to the boundary 9 of the through hole 4. The predetermined position is a position P1 at which an axis AXi passes through a center of gravity of the internal optical surface 7 and is parallel to the central axis AXo intersects the curved-surface area 8. Regarding the sign, either positive or negative, of the distance, the distance is let to be positive when the boundary 9 is positioned on the object side of the predetermined position.

As shown in FIG. 3A, Ds is the maximum outer diameter of the transparent resin member 1.

The image pickup member 5 is disposed in the through hole 4. In this case, it is possible to replace a surface PLi including the boundary 9 by the front-end surface of the image pickup member 5. Therefore, it is possible to let the front-end surface of the image pickup member 5 to be a reference at the time of calculating Ziax. Moreover, the transparent resin member 1 is provided to the front end of the insertion portion of the endoscope. It is possible to replace the central axis AXo and the axis AXi by an axis of the insertion portion. Therefore, it is possible to define Ziax by using the image pickup member 5 or the axis of the insertion portion as described below.

Conditional expression (1) is an expression indicating an appropriate displacement of the curved-surface area. Here, Ziax was defined as a parameter indicating a displacement in an axial direction of the curved-surface area at a position opposite to the internal optical surface. The center of gravity of the internal optical surface in the definition of Ziax coincides with a central axis when the internal optical surface has a circular shape. Therefore, Ziax is a displacement in an axial direction of the insertion portion at a position opposite to the center of gravity of the internal optical surface of the curved-surface area, and is a displacement with reference to a front-end surface of the image pickup member on the central axis of the internal optical surface.

The maximum outer diameter Ds of the transparent resin member is appropriate as a reference for a dimension of the endoscope insertion portion. Since Ziax has a dimension of length, it was standardized by the maximum outer diameter Ds of the transparent resin member.

In a case of falling below a lower limit value of conditional expression (1), a value of Ziax becomes excessively small. In this case, for the transparent resin member, the tapering tendency becomes inadequate. Consequently, the insertability is degraded.

A part of the illumination light reaches a peripheral portion of the opening of the through hole and an area around an outer peripheral portion of the outer surface after passing through the internal optical surface. In such place, it is difficult to control the angle of refraction optically. In a case of exceeding an upper limit value of conditional expression (1), the value of Ziax becomes excessively large. In this case, the position of the internal optical surface moves away from the opening of the through hole. As the position of the internal optical surface moves away from the opening of the through hole, the illumination light reaching the periphery of the opening of the through hole and the area around the periphery of the outer surface increases. As a result, the unevenness in the light distribution increases.

It is possible to express the change in the position of the internal optical surface with reference to the insertion portion of the endoscope. The one end of the insertion portion of the endoscope is provided with the transparent resin member and the other end thereof is provided with the operating portion. A side on which the operating portion is disposed is referred to as a hand side of the insertion portion. In the case of exceeding the upper limit value of conditional expression (1), the position of the internal optical surface is retracted excessively to the hand side of the insertion portion.

A preferable lower limit value of conditional expression (1) is 0.03. A preferable upper limit value of conditional expression (1) is 0.07. When the value of Ziax/Ds is in a range of 0.03 to 0.07, there is no inadequacy of the tapering tendency and no optically adverse effect due to retracting of the internal optical surface.

Next, Aiax in conditional expression (2) will be described below. The angle of inclination is an angle made by a tangent to the cross-sectional shape and an axis perpendicular to the central axis AXo. As shown in FIG. 3B, the plane PLi includes an axis perpendicular to the central axis AXo. Accordingly, the angle of inclination can be said to be an angle made by the tangent to the cross-sectional shape and the plane PLi.

Next, Aiax will be described below. Here, Aiax is an angle of inclination at a predetermined position. A cross section in this case, as shown by C-C in FIG. 3A, is a cross section which includes the central axis AXo and the predetermined position (position P1). Furthermore, out of points depicting the cross-sectional shape of the curved-surface area 8, Aiax is an angle of inclination at the position P1.

The image pickup member 5 is disposed in the through hole 4. In this case, it is possible to replace the central axis AXo by a central axis of the image pickup member 5. Therefore, it is possible to define Aiax by using the central axis of the image pickup member as described below.

Conditional expression (2) is an expression showing an appropriate angle of inclination of the curved-surface area. Here, Aiax is defined as a parameter which indicates a displacement in an axial direction of the curved-surface area at a position opposite to the internal optical surface. Similarly as Ziax in conditional expression (1), the center of gravity of the internal optical surface coincides with the central axis thereof when the internal optical surface has a circular shape. Therefore, Aiax is an angle of inclination at a position facing the center of gravity of the internal optical surface of the curved-surface area, in a shape in a cross section defined by a plane through which the central axis of the image pickup member passes, and is an angle of inclination on the central axis of the internal optical surface.

Moreover, Aiax is an angle of inclination at a position opposite to the internal optical surface on the outer surface. Consequently, Aiax has a strong effect on optical refraction and also has an effect on the tapering tendency.

In a case of falling below a lower limit value of conditional expression (2), the angle of inclination becomes excessively small. In this case, since the tapering tendency of the transparent resin member (insertion member) becomes inadequate, the insertability is degraded.

A plurality of members is disposed in the transparent resin member. A position of each of the plurality of members is determined upon taking into consideration the function and the effect. From the relationship with positions of other members, the internal optical surface is positioned at a location near an outer peripheral side of a center of the outer diameter of the transparent resin member. In this case, the predetermined position is a position near the outer periphery of the transparent resin member.

Falling below a lower limit value of conditional expression (2) signifies that a tangent at the predetermined position becomes almost perpendicular to the central axis. This means that in an area positioned near an outer periphery in the curved-surface area, a normal of the surface is close to parallel to the central axis. In other words, this area is a surface close to an end surface of a circular cylinder. When a proportion of the end surface of the circular cylinder occupying the curved-surface area is large, it is hard to say that the shape of the transparent resin member is tapered. Therefore, the insertability is degraded with such shape.

In a case of exceeding an upper limit value of conditional expression (2), since the angle of inclination becomes excessively large, the position of the internal optical surface moves away from the opening of the through hole. Or, the position of the internal optical surface is retracted excessively toward the hand side of the insertion portion. In this case, the refraction effect with respect to the illumination light at the curved-surface area becomes excessively strong.

In a case in which two non-through holes are formed to sandwich the through hole, illumination is carried out from both sides of the through hole. In this case, an area in which illumination light irradiated from one side and illumination light irradiated from the other side overlap (hereinafter, referred to as 'overlapping area'), is developed. When the refraction effect on the illumination light in the curved-surface area becomes excessively strong, the overlapping area is reduced. As a result, the light distribution near the boundary of the overlapping area is susceptible to be uneven.

A preferable lower limit value of conditional expression (2) is 16°. Moreover, a preferable upper limit value of conditional expression (2) is 32°. When the value of Aiax is in a range of 16° to 32°, there is no inadequate tapering tendency, no uneven light distribution, and no inadequate light distribution.

As described heretofore, according to the endoscope illuminating optical system according to the present embodiment, it is possible to realize an improvement in the insertability and a reduction of the uneven light distribution.

It is desirable that the endoscope illuminating optical system according to the present embodiment include a plurality of non-through holes, and at least two non-through holes are formed to be mirror-symmetric with respect to at least one of the cross-sections defined by a plane including the central axis.

By making such arrangement, symmetry of the light distribution is achieved. In an endoscope for urinary bladder, urinary bladder becomes the subject. The urinary bladder is an organ having a shape close to bilaterally symmetric. Therefore, in a wide angle observation of an inside of the urinary bladder, an observation in which an inner wall of a left side of the urinary bladder and an inner wall of a right side of the urinary bladder are captured near a left end and a right end respectively of an image, is envisaged. To be able to observe clearly from the inner wall of the left side of the urinary bladder up to the inner wall of the right side of the urinary bladder, it is desirable that the image pickup range be illuminated uniformly.

In such wide angle observation, an aspect ratio of the image pickup range is a horizontally long aspect ratio. In other words, a width in the leftward-rightward direction (horizontal direction) is more as compared to a width in the upward-downward direction (vertical direction). It is possible to illuminate such image pickup range from one direction. However, by illuminating from a plurality of directions, it is possible to illuminate more uniformly.

For such reasons, the endoscope illuminating optical system according to the present embodiment has the plurality of non-through holes. Accordingly, it is possible to dispose a plurality of lighting members in the transparent resin member. In this case, since the illumination is carried out from the plurality of directions, it is possible to illuminate more uniformly.

Moreover, at least two non-through holes are formed to be mirror-symmetric with respect to at least one cross-section defined by the plane including the central axis. By doing so, it is possible to irradiate illumination light from substantially symmetric positions with respect to the image pickup range. Therefore, it is possible to illuminate more uniformly.

In a case in which the number of non-through holes is odd, for example, when there are three non-through holes for example, two non-through holes are formed to be mirror-symmetric. The remaining one non-through hole may be formed at a position substantially equidistant from the two non-through holes. In FIG. 1B for example, it may be formed on a straight line depicted by A-A. Furthermore, a non-through hole maybe formed near the through hole.

In the endoscope illuminating optical system according to the present embodiment, it is desirable that the shape of the curved-surface area be axisymmetric, having an axis of symmetry near the central axis, and be able to be defined by a function expression in which a distance from the axis of symmetry is let to be a variable, and the following conditional expressions (3) and (4) be satisfied:

$$0.15 < Z[L]/Z[Ds/2] < 0.55 \quad (3), \text{ and}$$

$$0.4 < A[L]/A[Ds/2] < 0.8 \quad (4)$$

where,

Z [r] denotes a function expressing a displacement at a point on the curved-surface area, separated away only by a distance r from the axis of symmetry, and here the displacement is a distance when a distance up to a point on the curved-surface area was measured along the central axis with reference to the boundary, A [r] denotes a function expressing an angle of inclination based on a differential coefficient of Z [r] at the point on the curved-surface area, separated apart only by the distance r from the axis of symmetry, L denotes a distance from the axis of symmetry up to the center of gravity of the internal optical surface, and Ds denotes a maximum outer diameter of the transparent resin member.

In the endoscope illuminating optical system according to the present embodiment, the shape of the curved-surface area is axisymmetric, having an axis of symmetry near the central axis. Therefore, it is possible to calculate a displacement and an angle of inclination at a point on the curved-surface area with reference to a distance from the axis of symmetry.

Here, Z [r] is a function expressing the displacement, and the distance is let to be a variable. Moreover, Z [r] indicates a displacement at a point on the curved-surface area, away from the axis of symmetry only by the distance r. The displacement is a distance when the distance up to the point on the curved-surface area is measured along the central axis with reference to the boundary.

Furthermore, A [r] is a function expressing the angle of inclination, and the distance is let to be a variable. Here, A [r] indicates the angle of incidence based on a differential coefficient of Z [r] at the point on the curved-surface area, away from the axis of symmetry only by the distance r.

As mentioned above, it is possible to let the front-end surface of the image pickup member 5 to be a reference at the time of calculating the displacement and the angle of inclination. It is possible to replace the central axis AXo by an axis of the insertion portion. Therefore, it is possible to define Z [r] and A [r] by using the image pickup member 5 or the axis of the insertion portion as described below.

Moreover, Z [r] is a displacement in the axial direction of the insertion portion at the distance r from the axis of symmetry of the curved-surface area, and is a displacement with reference to the front-end surface of the image pickup member. Furthermore, A [r] is an angle of inclination based on the differential coefficient of Z [r] at the distance r from the axis of symmetry of the curved-surface area, and is an angle of inclination with reference to the front-end surface of the image pickup member Conditional expression (3) is an expression regulating the displacement tendency when the curved-surface area is defined by an axisymmetric function expression, on the basis of two displacement values. Moreover, Ziax defined by conditional expression (1) was a value determined independent of whether or not the surface shape is defined by a numerical expression.

Whereas, it is possible to calculate Z [L] and Z [Ds/2] in conditional expression (3) by replacing S in numerical expression (B) by L or Ds/2, when the surface shape has been defined in the form of numerical expression (A) for example. Moreover, it is also possible to calculate when numerical expression (A) has been replaced by another axisymmetric function expression.

Here, Z [L] corresponds to Ziax of conditional expression (1) replaced by a function expression. Moreover, Z [L] is obtained by substituting L for the variable r of the function Z [r]. Moreover, L is a distance from the axis of symmetry up to the center of gravity of the internal optical surface. Therefore, Z [L] indicates a displacement of a location opposite to the internal optical surface in the curved-surface area, or a displacement of the vicinity of that location. Consequently, a value of Z [L] has a significant effect on the optical characteristics.

Furthermore, Z [Ds/2] is obtained by substituting Ds/2 for the variable r of the function Z[r]. Here, Ds/2 is the maximum radius of the transparent resin member. Therefore, Z [Ds/2] indicates a displacement at a position of the maximum radius of the transparent resin member on the curved-surface area.

To put in another way, Z [Ds/2] is a displacement in the axial direction of the curved-surface area when the maximum radius of the transparent resin member was input as S in numerical expression (B). Here, Z [Ds/2] corresponds to a displacement when the central axis of the image pickup member and a center of the outer diameter of the transparent resin member were made to coincide tentatively. The displacement on the curved-surface area changes toward an outer peripheral side. Therefore, Z [Ds/2] becomes a parameter indicating the degree of displacement when the shape changes toward the outer peripheral side.

Moreover, Z [L]/Z [Ds/2] in conditional expression (3) is a value indicating a proportion of the displacement with a strong optical effect, standardized by the displacement toward the outer peripheral side. Therefore, Z [L]/Z [Ds/2] becomes an indicator for optimizing a tendency of shape variation in the curved-surface area.

When the value of Z [L]/Z [Ds/2] is relatively small, the shape of the curved-surface area becomes a shape displacing steeply from a location opposite to the internal optical surface toward the outer peripheral side. Consequently, the tapering tendency is weakened. Moreover, when the value of Z [L]/Z [Ds/2] is relatively large, the shape of the curved-surface area becomes a shape which is displaced steeply from the location facing the internal optical surface toward the image pickup member side. Consequently, the tapering tendency becomes stronger.

In a case of falling below a lower limit value of conditional expression (3), the change in the displacement from the location opposite to the internal optical surface toward the outer peripheral side becomes excessively steep in the shape of the curved-surface area. In this case, since the tapering tendency is inadequate, the insertability is degraded. Furthermore, when the shape changes steeply from the location opposite to the internal optical surface toward the outer peripheral side, a change in the refractive power in the vicinity thereof becomes large. Consequently, the light distribution becomes susceptible to be uneven.

In a case of exceeding an upper limit value of conditional expression (3), the shape changes steeply from the location opposite to the internal optical surface toward the image pickup member side. In this case, a change in the refractive power in the vicinity thereof becomes large. Consequently, the light distribution becomes susceptible to be uneven.

A preferable lower limit value of conditional expression (3) is 0.25. A preferable upper limit value of conditional expression (3) is 0.4. When the value Z[L]/Z[Ds/2] is in a range of 0.25 to 0.4, it is possible to suppress further the steep change in the shape, both from the location opposite to the internal optical surface toward the outer peripheral side or from the location opposite to the internal optical surface toward the image pickup member side. As a result, it is possible to suppress an excessive change in the refractive power caused due to the uneven light distribution.

Conditional expression (4) is an expression regulating a changing tendency of the angle of inclination when the curved-surface area has been defined by an axisymmetric function expression, on the basis of two values of the angle of inclination. Moreover, Aiax defined by conditional expression (2) was a value determined independent of whether or not the surface shape is defined by a numerical expression.

Whereas, it is possible to calculate A[L] and A[Ds/2] in conditional expression (4) by differentiating numerical expression (A) and replacing S by L or Ds/2 when the surface shape has been defined in the form of numerical expression (A) for example. Moreover, it is also possible to calculate A [L] and A [Ds/2] when numerical expression (A) has been replaced by another axisymmetric function expression.

Here, A [L] corresponds to Aiax of conditional expression (2) replaced by a function expression. Moreover, A [L] is obtained by substituting L for the variable r of the function A[r]. Therefore, A [L] indicates an angle of inclination of a location opposite to the internal optical surface in the curved-surface area, or an angle of inclination of the vicinity thereof. Consequently, a value of A [L] has a significant effect on the optical characteristics.

Furthermore, A [Ds/2] is obtained by substituting Ds/2 for the variable r of the function A[r]. Here, Ds/2 is the maximum radius of the transparent resin member. Therefore, A [Ds/2] indicates an angle of inclination of the curved-surface area at a position corresponding to the maximum radius of the transparent resin member. Moreover, A [Ds/2] corresponds to an angle of inclination when the central axis of the image pickup member and the center of the outer diameter of the transparent resin member were made to coincide tentatively. The angle of inclination on the curved-surface area changes toward the outer peripheral side. Therefore, A [Ds/2] becomes a parameter indicating an inclination tendency when the angle of inclination changes toward the outer peripheral side.

Moreover, A [L] and A [Ds/2] in conditional expression (4) is a value indicating a proportion of the angle of inclination with a strong optical effect, standardized by the angle of inclination toward the outer peripheral side. Therefore, similarly as conditional expression (3), A [L]/A [Ds/2] becomes another indicator for optimizing a tendency of shape variation in the curved-surface area.

Similar to the case of conditional expression (3), when the value of A [L]/A [Ds/2] is relatively small, the shape of the curved-surface area becomes a shape which is displaced steeply from a location opposite to the internal optical surface toward the outer peripheral side. Consequently, the tapering tendency is weakened. Moreover, when the value of A [L]/A [Ds/2] is relatively large, the shape of the curved-surface area becomes a shape displacing steeply from the location facing the internal optical surface toward the image pickup member side. Consequently, the tapering tendency becomes stronger.

In a case of falling below a lower limit value of conditional expression (4), the change in the angle of inclination from the location opposite to the internal optical surface toward the outer peripheral side becomes excessively steep in the shape of the curved-surface area. In this case, since the tapering tendency is inadequate, the insertability is degraded.

Furthermore, when the angle of inclination changes steeply from the internal optical surface toward the outer peripheral side, a change in the refractive power in the vicinity thereof becomes large. Consequently, the light distribution becomes susceptible to be uneven.

In a case of exceeding an upper limit value of conditional expression (4), the angle of inclination changes steeply from the location opposite to the internal optical surface toward the image pickup member side. In this case, a change in the refractive power in the vicinity thereof becomes large. Consequently, the light distribution becomes susceptible to be uneven.

A preferable lower limit value of conditional expression (4) is 0.5. Moreover, a preferable upper limit value of conditional expression (4) is 0.75. When even more desirable value A [L]/A [Ds/2] is in a range of 0.5 to 0.75, it is possible to suppress further the steep change in the angle of inclination both from the location opposite to the internal optical surface toward the outer peripheral side or from the location opposite to internal optical surface toward the image pickup member side. As a result, it is possible to suppress an excessive change in the refractive power caused due to the uneven light distribution.

In the endoscope illuminating optical system according to the present embodiment, it is desirable that the curved-surface area be a spherical surface or an aspheric surface having an axis of symmetry near the central axis, and the following conditional expression (5) be satisfied:

$$0.55 < Roax/Ds < 2 \quad (5)$$

where,

Roax denotes one of an absolute value of a radius of curvature at a central portion of the spherical surface or an absolute value of a radius of curvature of a central portion of the aspheric surface, and Ds denotes the maximum outer diameter of the transparent resin member.

It is desirable that the curved-surface area be a spherical surface or an aspheric surface. Moreover, it is desirable that both the spherical surface and the aspheric surface have an axis of symmetry near the central axis. Conditional expression (5) is an expression regulating a desirable absolute value of the radius of curvature when a spherical surface or an aspheric surface is used.

Since Roax has a dimension of length, it was standardized by the maximum outer diameter Ds of the transparent resin member similarly as in the case of conditional expression (1).

Regarding the shape of the curved-surface area, desirable conditions of displacement and angle of inclination at an optically significant position were regulated by conditional expression (1) and conditional expression (2). Moreover, assuming that the shape of the curved-surface area is axisymmetric and can be defined by a function, in conditional expression (3) and conditional expression (4), desirable conditions related to changing tendency of the displacement and angle of inclination in the curved-surface area were regulated.

Conditional expression (5) is a preferable condition for a case in which the shape of the curved-surface area is restricted to a spherical shape or an aspheric shape. For a spherical surface or an aspheric surface, radius of curvature at a central portion is a basic parameter. Here, Roax is an appropriate parameter for regulating the displacement, the angle of inclination, and changing tendency thereof together.

When a value of Roax/Ds is relatively small, the curved-surface area assumes an acute convex shape. In this case, since the tapering tendency becomes stronger, the insertability improves. However, since a positive refractive power of the curved-surface area becomes large, there is an optically adverse effect of narrowing of an angle of light distribution. Furthermore, a position of the internal optical surface moves away from the opening of the through hole. As the position of the internal optical surface moves away from the opening of the through hole, the illumination light reaching the periphery of the opening of the through hole and the area around the periphery of the outer surface increases. As a result, the unevenness in the light distribution increases.

To put in another way, since the lighting member and the internal optical surface are retracted toward the hand side of the insertion portion, light reaching portions such as a peripheral portion of the image pickup member increases.

Moreover, when the value of Roax/Ds is relatively high, the tapering tendency is weakened. In this case, the insertability is degraded.

In a case of falling below a lower limit value of conditional expression (5), there is an optically adverse effect of narrowing the angle of light distribution. Furthermore, the position of the internal optical surface moves away from the opening of the through hole. As the position of the internal optical surface moves away from the opening of the through hole, illumination light reaching the periphery of the opening of the through hole and the area around the periphery of the outer surface increases. As a result, the unevenness in the light distribution increases.

To put in another words, since the lighting member and the internal optical surface are retracted toward the hand side of the insertion portion, light reaching portions such as the peripheral portion of the image pickup member increases. At the image pickup member and the outer peripheral portion, it is difficult to control refractivity optically.

In a case of exceeding an upper limit value of conditional expression (5), the tapering tendency becomes excessively weak. In this case, the insertability is degraded.

A preferable lower limit value of conditional expression (5) is 0.6. Moreover, a preferable upper limit value of conditional expression (5) is 1.2. When the value of Roax/Ds is in a range of 0.6 to 1.2, it is possible to balance favorably the tapering tendency and optical characteristics.

Here, a desirable arrangement of the endoscope illuminating optical system according to the present embodiment is summarized below.

The endoscope illuminating optical system according to the present embodiment includes, the transparent resin member having a function of holding the image pickup member at the front end of the insertion portion and an illuminating optical function, and the transparent resin member has the internal optical surface on an inner-surface side thereof, on which the illumination light is made to be incident, and has the light guide or the light emitter at a position opposite to the internal optical surface, which outputs the illumination light, and has the curved-surface area on the outer surface of the transparent resin member, which makes the illumination light via the internal optical surface output to the object space, and the curved-surface area has the shape displaced from the vicinity of the boundary with the image pickup member to the hand side of the insertion portion toward the outer periphery of the insertion portion, and regarding the shape in the cross-section defined by a plane through which the central axis of the image pickup member passes, it is desirable that the shape be such that at least in the orientation from the central axis toward the internal optical surface, the displacement and the angle of inclination increase continuously and monotonously as drawn away from the central axis of the image pickup member toward the outer periphery, and the conditional expressions (1) and (2) be satisfied.

It is desirable that the internal optical surface, the light guide or the emitter, and the curved-surface area be mirror-symmetric with respect to at least one of the cross sections defined by the plane through which the central axis of the image pickup member passes.

It is desirable that the arrangement be such that the displacement of the curved-surface area in the axial direction of the insertion portion has the axisymmetric shape having the axis of symmetry near the central axis of the image pickup member, and can be defined by the function expression in which the distance from the axis of symmetry is let to be a variable, and conditional expression (3) and (4) be satisfied.

Furthermore, it is desirable to satisfy conditional expression (5) in a case in which the curved-surface area is a spherical surface or an aspheric surface having the axis of symmetry near the central axis of the image pickup member.

Examples of the endoscope illuminating optical system will be described below in detail with reference to the accompanying diagrams. However, the present invention is not restricted to the examples described below.

Figure 4A:
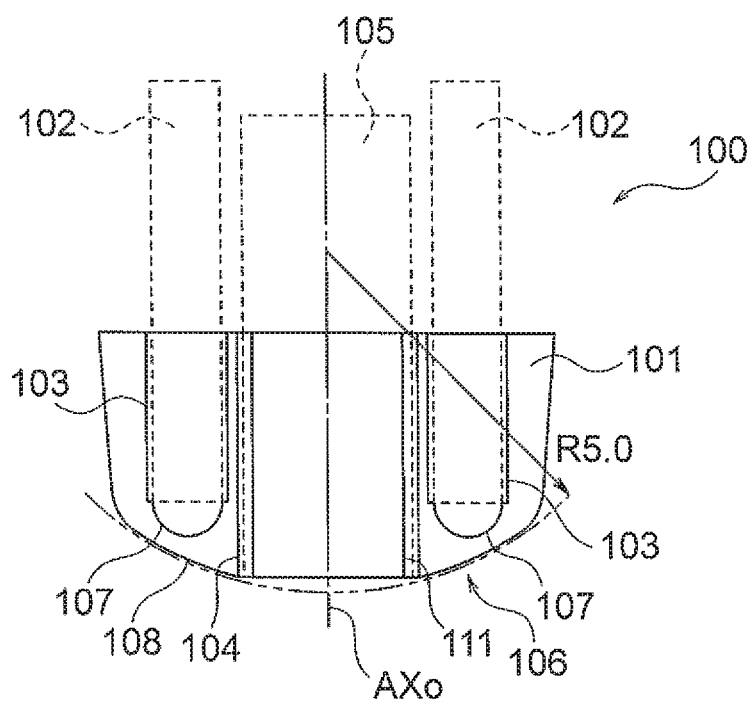
FIG. 4A, FIG. 4B, and FIG. 4C are schematic diagrams showing an arrangement of an endoscope illuminating optical system according to an example 1.
Figures 4B, 4C:
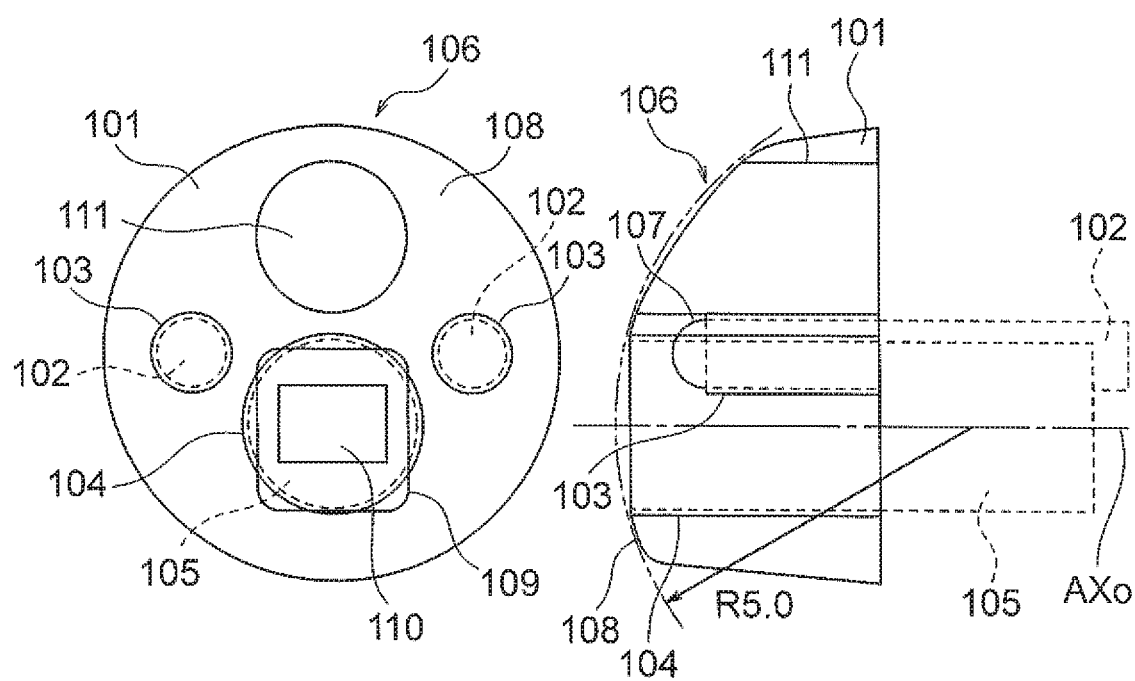
Figure 17A:
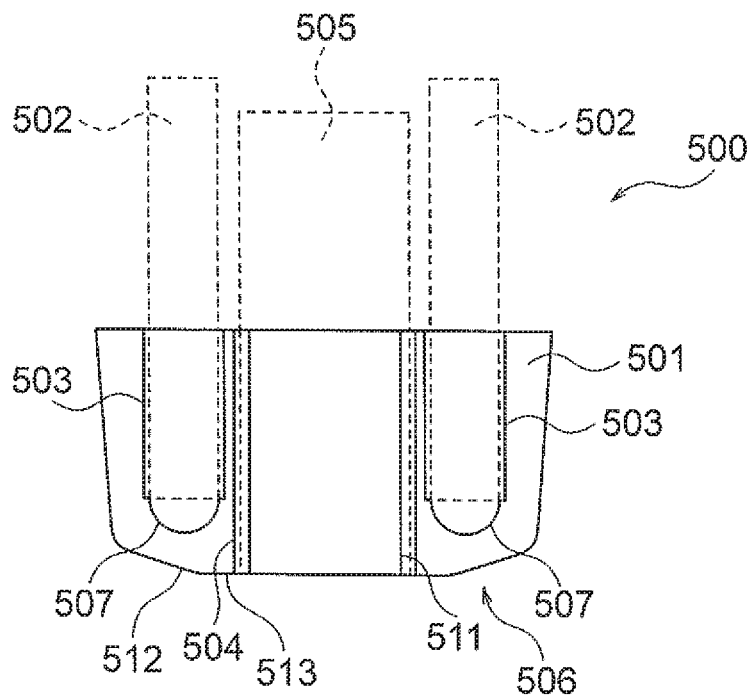
FIG. 17A, FIG. 17B, and FIG. 17C are is schematic diagrams of an arrangement of an endoscope illuminating optical system according to an example for comparison.
Figure 17B:
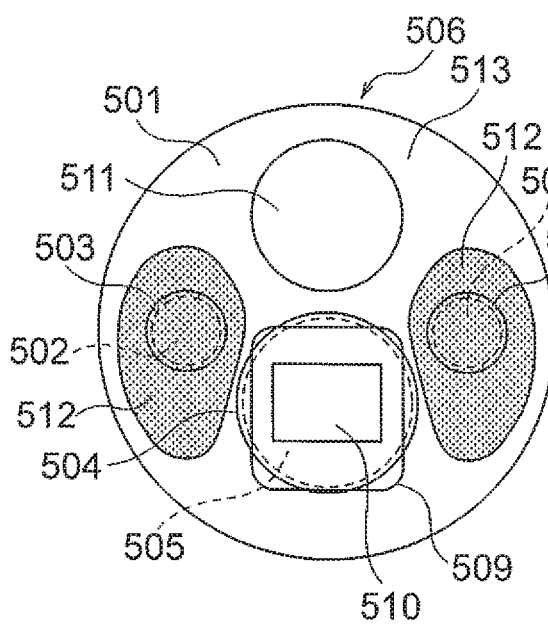
Figure 17C:
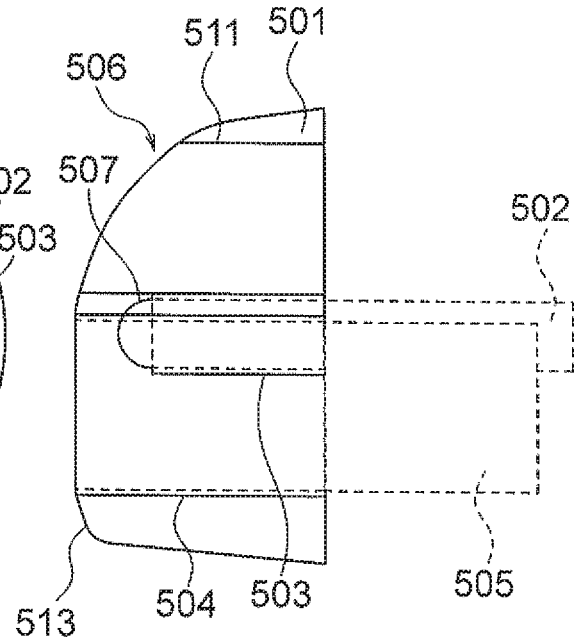

The description will be made while comparing an endoscope illuminating optical system according to an example 1 and an endoscope illuminating optical system according to an example for comparison. FIG. 4A, FIG. 4B, and FIG. 4C are schematic diagrams showing an arrangement of the endoscope illuminating optical system according to the example 1. FIG. 4A is a top view, FIG. 4B is a front view, and FIG. 4C is a side view. FIG. 17A, FIG. 17B, and FIG. 17C are schematic diagrams showing an arrangement of the endoscope illuminating optical system according to the example for comparison. FIG. 17A is a top view, FIG. 17B is a front view, and FIG. 17C is a side view. Description in detail of arrangements same as in the abovementioned endoscope illuminating optical system is omitted.

The example 1 will be described below. An endoscope illuminating optical system 100 is to be disposed at a front end of an insertion portion an endoscope. The endoscope illuminating optical system 100 includes a transparent resin member 101 and a lighting member 102.

A shape of the transparent resin member in a cross section orthogonal to the central axis AXo is substantially circular. A non-through hole 103 and a through hole 104 are formed in the transparent resin member 101. The non-through hole 103 is a hole for disposing the lighting member 102. The through hole 104 is a hole for disposing an image pickup member 105.

In the non-through hole 103, the hole does not reach an outer surface 106 of the transparent resin member 101. An internal optical surface 107 is formed at an interior of the transparent resin member 101, at a position opposite to the lighting member 102. A shape of the internal optical surface 107 is concave toward the image side. Moreover, a curved-surface area 108 is positioned on the outer surface 106, at a position opposite to the internal optical surface 107.

The image pickup member 105 has an observation function. The image pickup member 105 includes a solid image pickup element 109 and an objective optical system (not shown in the diagram). The solid image pickup element 109 has an image pickup surface. In FIG. 4B, an image pickup effective range 110 on an image pickup surface is shown by a rectangular shape. The objective optical system forms an object image on the image pickup surface. In FIG. 4B, an upward-downward direction (vertical direction) corresponds to a vertical direction of image, and a leftward-rightward direction (horizontal direction) corresponds to a horizontal direction of image. The solid image pickup element 109 outputs a signal of an image having a horizontally long aspect ratio.

A channel opening 111 is formed in the transparent resin member 101. Generally, a channel has been known as a path for inserting a treatment tool. In an endoscope for urinary organs, a turbid liquid such as urine becomes an obstacle in observation. Therefore, it is necessary to replace the turbid liquid by a highly transparent liquid such as a physiological saline solution. The replacement is called as perfusion, and a channel is used in the perfusion as well.

A diameter of the channel opening 111 is extremely important as it affects both of a perfusion capability and a treatment performance. In an endoscope for urinary bladder, a channel diameter not less than 2 mm is necessary for an endoscope outer diameter of about 6.5 mm.

In a diameter of the transparent resin member 101, the solid image pickup element 109 and the channel opening 111 are structures having a large cross-sectional area. When the solid image pickup element 109 and the channel opening 111 are disposed in the upward-downward direction, a space in which the lighting member 102 can be disposed is restricted to a space in the leftward-rightward direction.

In a case of using a light guide as the lighting member 102, a light guide having a front end bifurcated into two is disposed at the interior of the transparent resin member 101. In the transparent resin member 101, it is possible to dispose these two light guides symmetrically with respect to a line connecting the image pickup member 105 and an axis of the channel opening 111.

In a cross section of an outer diameter of the transparent resin member 101, it is desirable that positions of the lighting member 102 and the internal optical surface 107 be separated apart from portions of which, the shape is determined by non-optical constraints such as the channel opening 111, the image pickup member 105, and the outer peripheral portion. Moreover, it is desirable that the positions of the lighting member 102 and the internal optical surface 107 maintain an appropriate distance from the image pickup member 105.

When the lighting member 102 and the internal optical surface 107 are retracted excessively toward the hand side of the insertion portion, light reaching the portions for which, it is difficult to control the refractivity optically, such as the image pickup member 105, the channel opening 111, and the outer peripheral portion, increases. Moreover, when the lighting member 102 and the internal optical surface 107 are excessively close to the image pickup member 105, light directed to the image pickup member 105 is shielded by the image pickup member 105. Therefore, it is desirable that at a position in a cross section of an outer diameter of the image pickup member 105 and the channel opening 111, the lighting member 102 and the internal optical surface 107 be positioned near the midpoint of an outer periphery and a boundary portion of the image pickup member 105 near the vertical center of the transparent resin member 101.

Here, 'R 5.0' in FIG. 4A and FIG. 4C indicates that the curved-surface area 108 is a spherical surface having a radius of curvature 5.0 mm. The spherical surface has a center of curvature on the central axis AXo of the image pickup member 105. A position of the center of curvature of the spherical surface is determined to be such that the spherical surface makes a contact near an outer periphery of the image pickup member 105.

The curved-surface area 108 has a shape which is displaced toward the hand side of the insertion portion, directed from the area near the boundary with the image pickup member 105 toward the outer periphery of the insertion portion, and a shape such that, in the orientation directed toward the internal optical surface 107 from the central axis AXo of the image pickup member 105, the displacement and the angle of inclination increase continuously and monotonously with being directed toward the outer periphery from the central axis AXo of the image pickup member 105.

Furthermore, the endoscope illuminating optical system 100 satisfies conditional expressions (1) and (2). Therefore, in the endoscope illuminating optical system 100, it is possible to realize an improvement in the insertability and a reduction of uneven light distribution.

In the in-water observation, the object space is filled with water. Therefore, refraction of light emerged from the curved-surface area 108 to the object space is determined in accordance with a difference in a refractive index of the transparent resin member 101 and the refractive index of water. As a material of the transparent resin member 101, various materials having a high refractive index as well as high transmittance of the visible range, and also having a high durability are to be used. Examples of such materials are polysulfone resins (typical refractive index 1.635) or polyphenyl sulfone resins (typical refractive index 1.675).

For these materials, the refractive index being higher than the refractive index of water (1.333), refraction occurs between the curved-surface area 108 and water. Since the curved-surface area 108 has a spherical shape which is convex toward the object side, it has a positive refractive power even for the in-water observation. In such manner, the curved-surface area 108 has a light-focusing refraction effect. Therefore, the curved-surface area 108 does not have an effect of widening the light distribution by diffusing the illumination light.

The example for comparison will be described below. An endoscope illuminating optical system 500 includes a transparent resin member 501 and a lighting member 502. A non-through hole 503 and a through hole 504 are formed in the transparent resin member 501. A lighting member 502 is disposed in the non-through hole 503, and an image pickup member 505 is disposed in the through hole 504.

The image pickup member 505 includes a solid image pickup element 509. The solid image pickup element 509 has an image pickup surface. In FIG. 17B, an image pickup effective range 510 on the image pickup surface is shown by a rectangular shape.

An internal optical surface 507 is formed at an interior of the transparent resin member 501. Moreover, a channel opening 511 is formed in the transparent resin member 501. Furthermore, an outer surface 506 includes an inclined flat surface portion 512 and a non-optical shaped portion 513.

In the example for comparison, except for a shape of the outer surface 506 of the transparent resin member 501 and a position in an axial direction of an insertion portion of the internal optical surface 507 dependent on the shape of the outer surface 506, an arrangement of the endoscope illuminating optical system is same as the arrangement of the endoscope illuminating optical system in the example 1. A shape of the internal optical surface 507 and the lighting member 502 being same, light distribution characteristics of illumination light before being refracted at an outer surface are same in the example for comparison and examples 1 to 4.

As mentioned above, in the example 1, the outer surface 106 of the transparent resin member 101 includes the curved-surface area 108. The curved-surface area 108 has a shape which is displaced toward the hand side of the insertion portion, directed form the area near the boundary with the image pickup member 105 toward the outer periphery of the insertion portion, and a shape such that, in the orientation directed toward the internal optical surface 107 from the central axis AXo of the image pickup member 105, the displacement and the angle of inclination increase continuously and monotonously with being directed toward the outer periphery from the central axis AXo of the image pickup member 105. Moreover, the curved-surface area 108 satisfies conditional expressions (1) and (2).

Moreover, the curved-surface area 108 is a spherical surface having a radius of curvature 5.0 mm. In the curved-surface area 108, the spherical surface having a radius of curvature 5.0 occupies almost a front-end outer surface. The shape of the transparent resin member 101 being a smooth tapered shape, the insertability is favorable.

Therefore, in the example 1, it is possible to realize an improvement in the insertability and a reduction of the uneven light distribution.

Whereas, in the example for comparison, the outer surface 506 of the transparent resin member 501 is divided into the inclined flat surface portion 512 and the non-optical shaped portion 513. The inclined flat surface portion 512 is inclined by 15° toward the center side of the image pickup member 505. Therefore, the transparent resin member 501 has a slightly tapered shape.

The inclined flat portion 505 positioned as an optically effective range on the outer surface 506 side. By modelling this unusual effective range as an inclined flat surface by an optical design software, a simplified optical design of the unusual effective range is possible. However, the example for comparison has a flaw of being susceptible to uneven light distribution due to the shape of the outer surface 506.

The cause of uneven light distribution is that the non-optical shaped portion 513 exists with an unignorable area at a position relatively closer to the internal optical surface 507 and there is a high discontinuity with regard to refraction at the inclined flat surface portion 512 and the non-optical shaped portion 513.

Furthermore, it is difficult to say that a shape of the transparent resin member 501 of the example for comparison is tapered, and the shape is angular. Consequently, the insertability is inferior to the insertability when the transparent resin member 101 of the example 1 is used.

Figure 5:
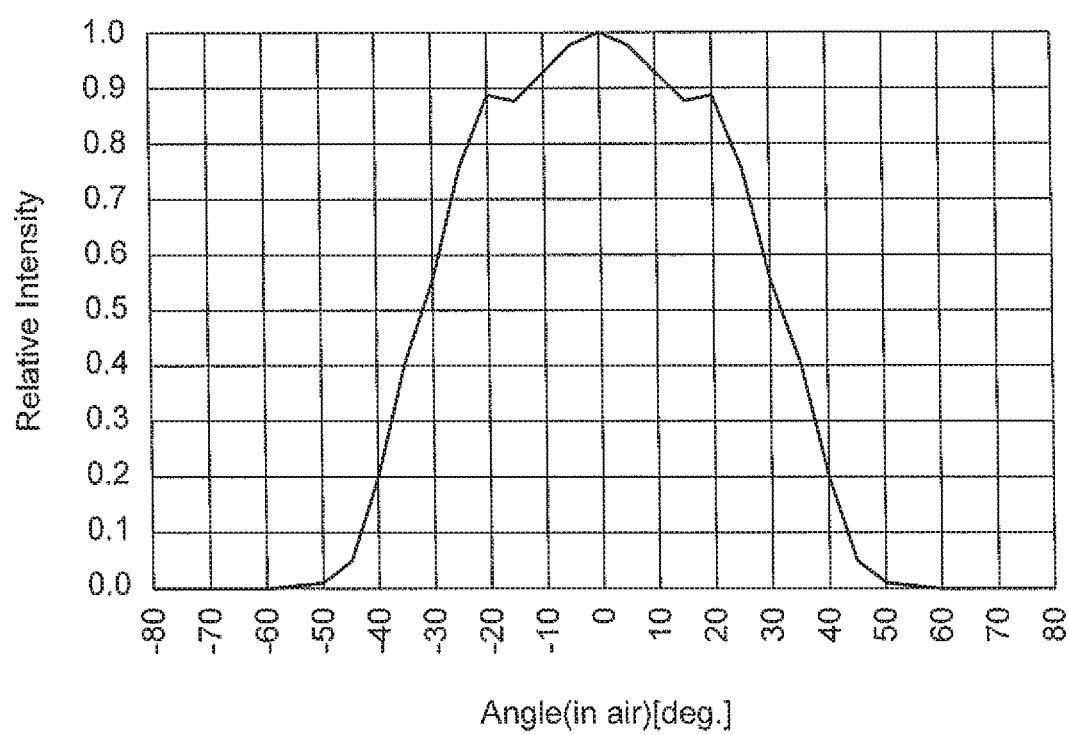
FIG. 5 is a diagram showing light distribution characteristics of light emerged from a light guide.

Next, the illumination light in the object space will be described below. In both of the example 1 and the example for comparison, light distribution characteristics of light emerged from the light guide are same. FIG. 5 is a diagram showing the light distribution characteristics of light emerged from the light guide.

Light having the light distribution characteristics shown in FIG. 5 is used as light-source data for simulation. It is assumed that light having a light-distribution angle of about 80° is emerged from the light guide. Even in examples 2 to 4 that will be described later, a light guide having the light distribution characteristics shown in FIG. 5 is used.

Figure 6A:
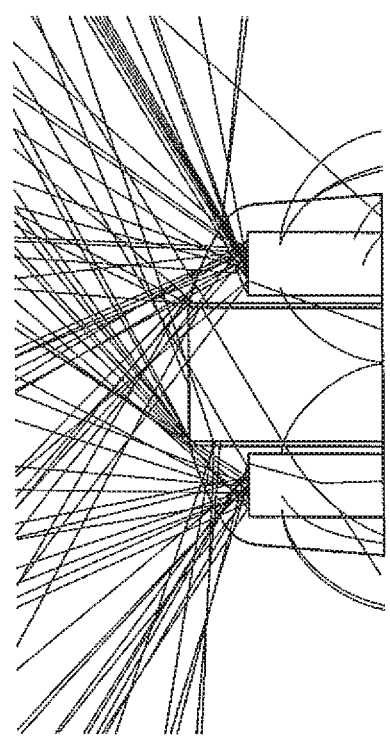
FIG. 6A and FIG. 6B are diagrams showing an illumination light in the endoscope illuminating optical system according to the example 1.
Figure 6B:
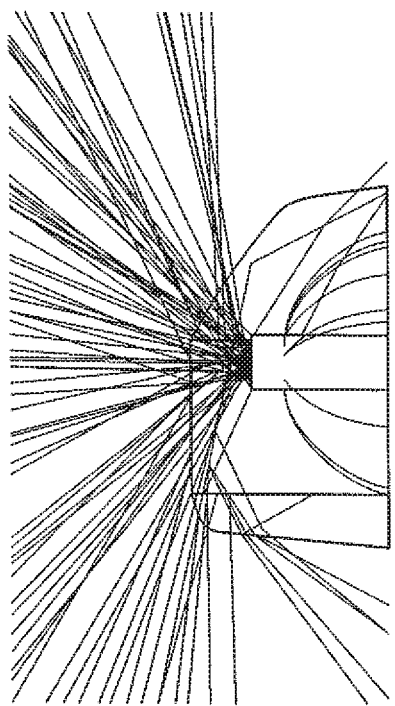
Figure 7:
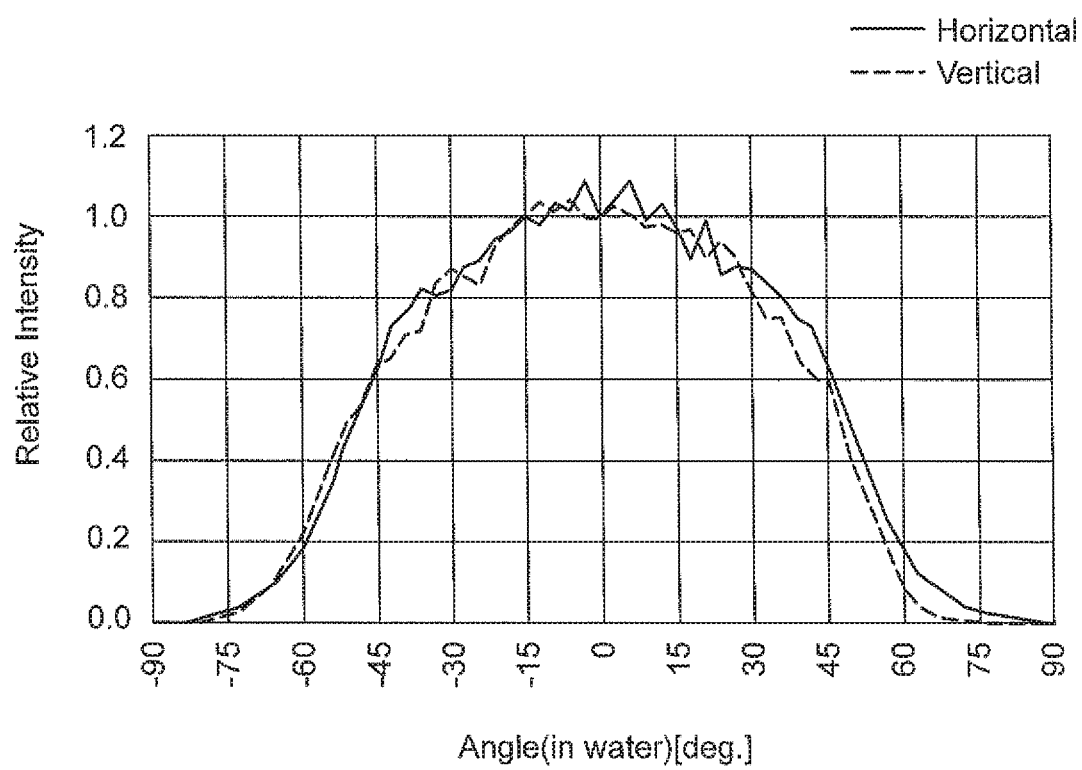
FIG. 7 is a graph showing light distribution characteristics in water of the example 1.

FIG. 6A and FIG. 6B are diagrams showing illumination light in the endoscope illuminating optical system according to the example 1. FIG. 6A is a light-ray diagram showing diffusion of light rays in the horizontal direction and FIG. 6B is a light-ray diagram showing diffusion of light rays in the vertical direction. FIG. 7 is a graph showing light distribution characteristics in water of the example 1.

Figure 18A:
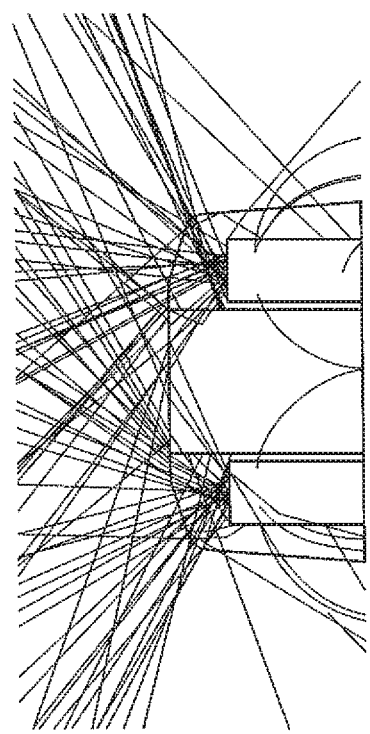
FIG. 18A and FIG. 18B are diagrams showing illumination light in the endoscope illuminating optical system of the example for comparison.
Figure 18B:
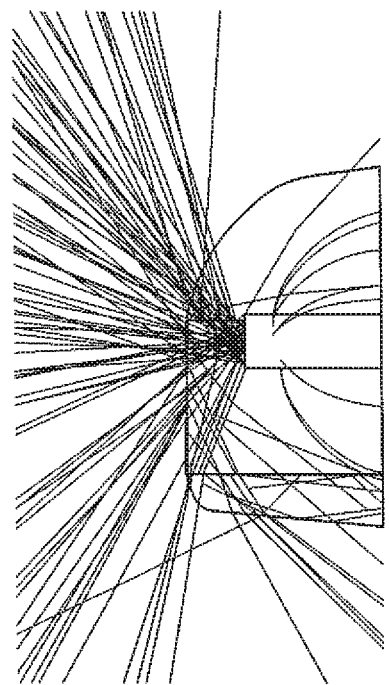
Figure 19:
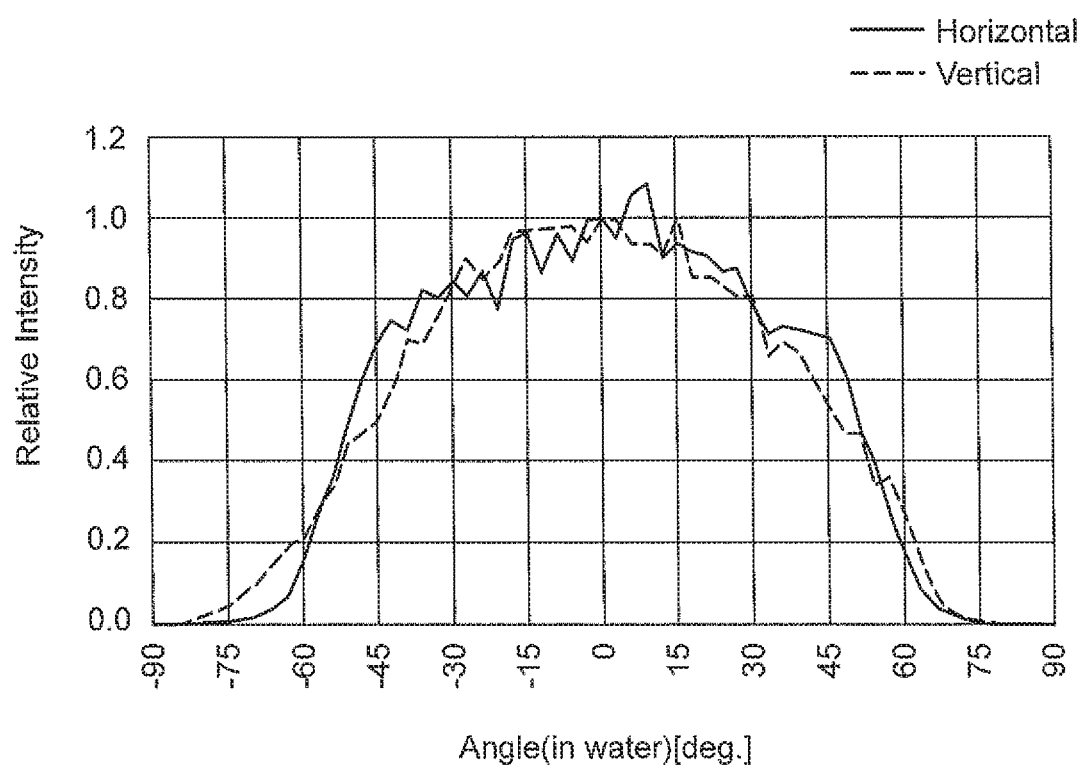
FIG. 19 is a graph showing light distribution characteristics in water of the example for comparison.

FIG. 18A, and FIG. 18B are diagrams showing illumination light in the endoscope illuminating optical system according to the example for comparison. FIG. 18A is a light-ray diagram showing diffusion of light rays in the horizontal direction and FIG. 18B is a light-ray diagram showing diffusion of light rays in the vertical direction. FIG. 19 is a graph showing light distribution characteristics in water of the example for comparison.

In the light-ray diagrams of the example 1 and the light-ray diagrams of the example for comparison, as to how the light rays are emerged in water is shown. Moreover, in the light-distribution graph, the horizontal axis indicates an angle in water, the vertical axis indicates a relative intensity, a solid line indicates light distribution characteristics in the horizontal direction, and a dashed line indicates light distribution characteristics in the vertical direction. Moreover, for the light distribution characteristics, far-field angle distribution in water is obtained by simulation by Monte Carlo method, and a direction of 0° is standardized as 1. Similar is true for the examples 2 to 4 that will be described later.

According to the light-ray diagrams in FIG. 6A and FIG. 6B, in the example 1, light is diffused almost evenly in both the horizontal direction and the vertical direction, to be directed toward the object space in water. FIG. 6A and FIG. 6B are diagrams in which a small number of light rays that are not blackout on display are selected from a result of a large number of light rays tracked by Monte Carlo method. Therefore, high or low of light-ray density does not express the strength of the intensity distribution and uneven light distribution.

On the other hand, regarding the example for comparison, even upon comparing with the diffusion of light rays in the example 1, no difference in particular is found. In other words, only from the light-ray diagrams shown in FIG. 18A and FIG. 18B, a difference from the example 1 is not clear. However, in a graph of light distribution in water shown in FIG. 19, an adverse effect on the uneven light distribution due to the non-optical shaped portion 513 is seen notably. Therefore, the description will be made by using the light-distribution graph.

According to the light-distribution graph in FIG. 7, in the example 1, the relative intensity varies smoothly in a range of ±90°. The relative intensity varies smoothly in both the horizontal direction and the vertical direction. Moreover, a difference between the relative intensity in the horizontal direction and the relative intensity in the vertical direction is not large for each angle.

On the other hand, according to the light-distribution graph in FIG. 19, in the example for comparison, a shoulder portion is formed near +45° in the horizontal direction. At the shoulder portion, for the relative intensity which increased smoothly from 60° to 45°, the increase in the relative intensity has become slight from 45° to 30°. This indicates that there is a tendency of collectinf light of high intensity in this angular direction.

Moreover, the difference between relative intensity in the horizontal direction and the relative intensity in the vertical direction has become large near ±45°. Near ±45°, the relative intensity in the horizontal direction is more than the relative intensity in the vertical direction.

Figure 20:
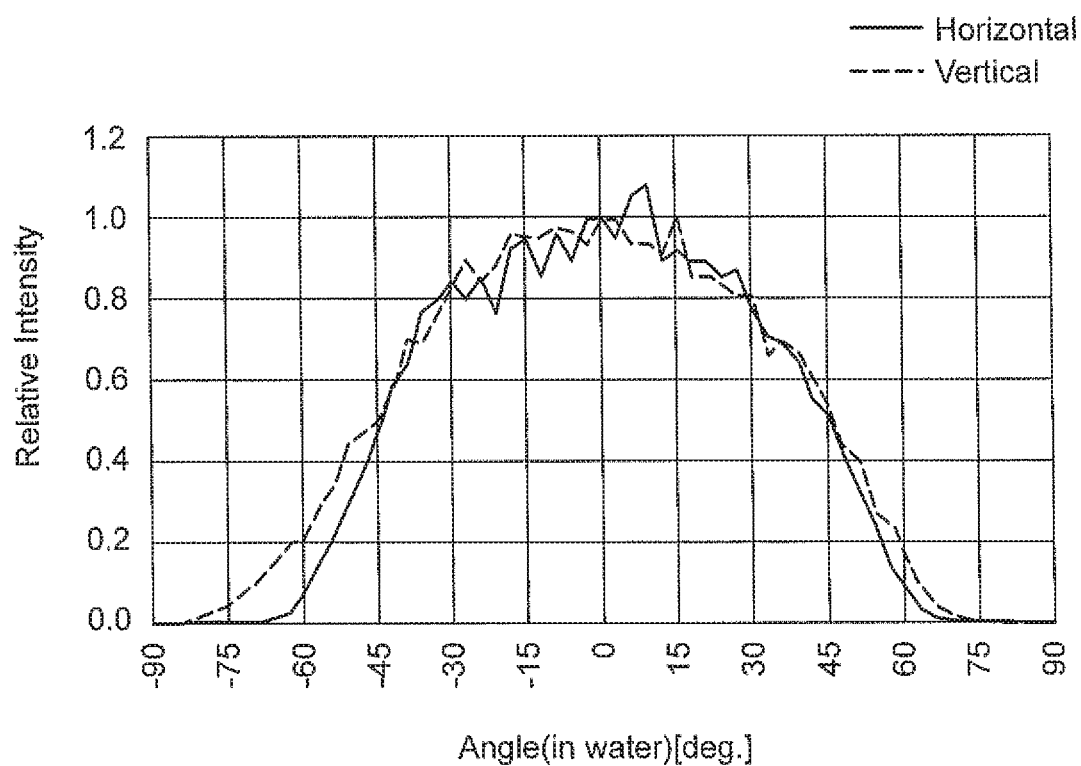
FIG. 20 is a light distribution graph of the example for comparison.

FIG. 20 also is a light-distribution graph of the example for comparison. In FIG. 20, the non-optical shaped portion 513 is subjected to light shielding, and the illumination is carried out only by the inclined flat surface portion 512. From the light-distribution graph shown in FIG. 20, an angle at which, and an intensity with which, the light emerged from the inclined flat surface portion 512 was directed to the illumination range becomes evident. In the light-distribution graph shown in FIG. 20, no shoulder is formed near +45° in the horizontal direction. Moreover, the difference between the relative intensity in the horizontal direction and the relative intensity in the vertical direction has not become large near ±45°.

Figure 21:
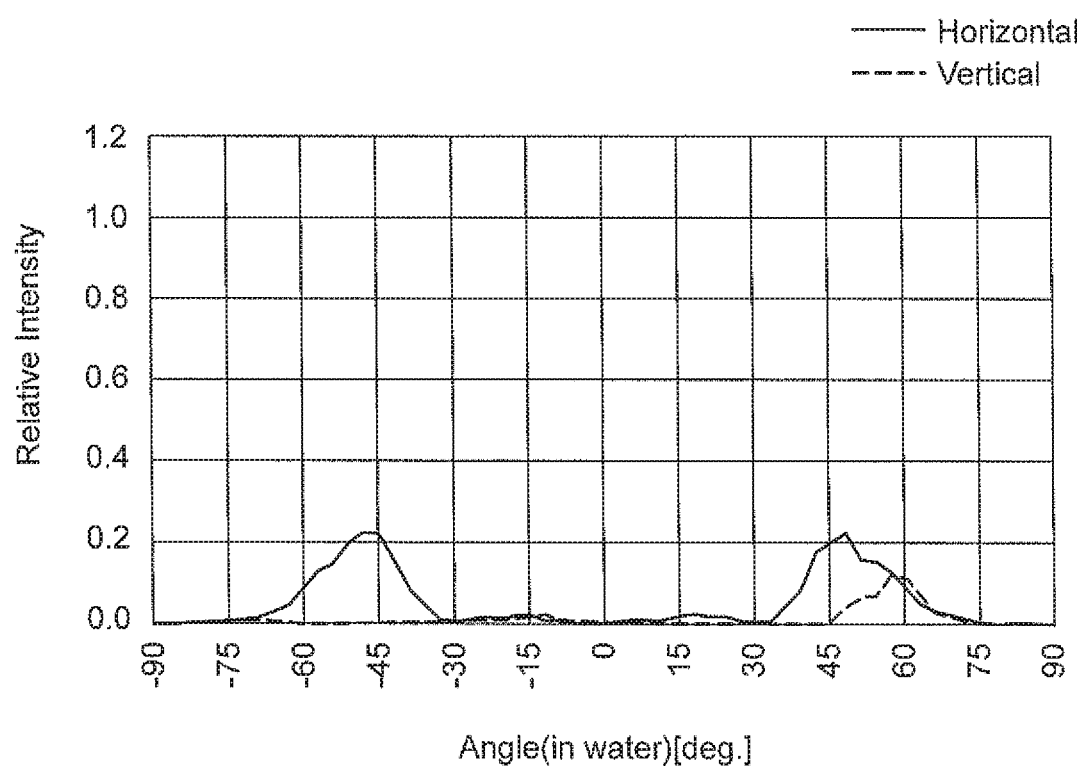
FIG. 21 is a light distribution graph of the example for comparison.

FIG. 21 also is a light-distribution graph of the example for comparison. In FIG. 21, the inclined flat surface portion 512 is subjected to light shielding, and the illumination is carried out only by the non-optical shaped portion 513. From the light-distribution graph shown in FIG. 21, an angle at which, and an intensity with which, the light emerged from the non-optical shaped portion 513 was directed to the illumination range becomes evident.

In the light-distribution graph shown in FIG. 21, the relative intensity near ±45° in the horizontal direction has become high (large). The relative intensity is at the peak at ±45°. It is evident that the relative intensity at the peak is 20% of the relative intensity in the direction of 0° in the light-distribution graph shown in FIG. 19. The light having the relative intensity near ±45° may be considered to be light that has caused shoulder near ±45° in the horizontal direction in the light-distribution graph shown in FIG. 19.

In such manner, light emerged from the non-optical shaped portion 513 is light which is deemed as unnecessary light. This light is considered to have formed the uneven light distribution.

When the light-distribution graph of the example 1 and the light-distribution graph of the example for comparison are compared, the light-distribution graph of the example 1 has no shoulder as seen in the light-distribution graph of the example for comparison. Therefore, in the endoscope illuminating optical system according to the example 1, there is no uneven light distribution that may become a tangible damage.

Moreover, as shown in FIG. 20, when the non-optical shaped portion 513 is subjected to light shielding, it is possible to make the uneven light distribution disappear. However, in this case, as it is evident from the light-distribution graph, an angle of light distribution in the horizontal direction becomes narrow as compared to that in the example 1. In such manner, in the endoscope illuminating optical system according to the example 1, the angle of light distribution not smaller than 45° in the horizontal direction has been secured. Therefore, in this regard, the endoscope illuminating optical system according to the example 1 is superior. The reason for this is that the curved-surface area 108 has a smooth shape at which the uneven light distribution does not occur, and it is possible to enlarge the optically effective range.

In the light-distribution graph shown in FIG. 7, a ripple is observed in a range of ±40°. The ripple is an error which depends on the number of light rays of the Monte Carlo method. Therefore, the ripple does not form the uneven light distribution.

In the example for comparison, the inclined flat surface portion 512 corresponds to the optically effective range. In the example for comparison, the shape is such that the inclined flat surface portion 512 and the non-optical shaped portion 513 are separated. Therefore, it is not possible to avoid the uneven light distribution occurring due to the discontinuity.

It is evident from simulation that it is possible to suppress the uneven light distribution if light to the non-optical shaped portion 513 is shielded. However, within a range of size sought for the endoscope front-end portion, in the transparent resin member, it is not practical to carry out multistep combined forming in which a light-shielding member is added. The worth of the transparent resin member is in manufacturability of a small-size and complex shape in which a frame function and an optical function are combined by a capability to integrate the transparent resin member into one transparent material.

In the example for comparison, as a method for reducing the uneven light distribution without changing a shape of the outer surface 506 side of the transparent resin member 501, reducing unnecessary light that causes the uneven light distribution by passing through the non-optical shaped portion 513, by devising an idea for the internal optical surface 507 may be considered.

Specifically, a diverging effect at the internal optical surface 507 is to be weakened. By doing so, since a proportion of light passing through the inclined flat surface portion 512 increases, a proportion of light passing through the non-optical shaped portion 513 decreases relatively. However, since the light distribution angle becomes narrow in this method, it is not possible to realize an adequate light distribution angle suitable for wide-angle observation in water. Therefore to achieve both of securing the light distribution necessary for the wide-angle observation in water and avoiding the uneven light distribution, as shown in the curved-surface area 108 in the example 1, it is indispensable to devise an idea for the shape of the outer surface 106.

Figure 8A:
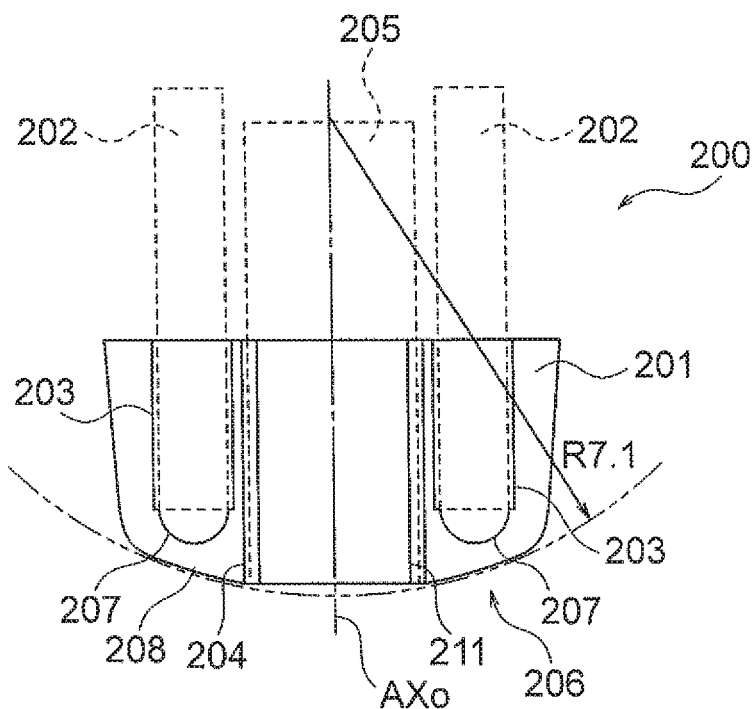
FIG. 8A, FIG. 8B, and FIG. 8C are schematic diagrams showing an arrangement of an endoscope illuminating optical system according to an example 2.
Figure 8B:
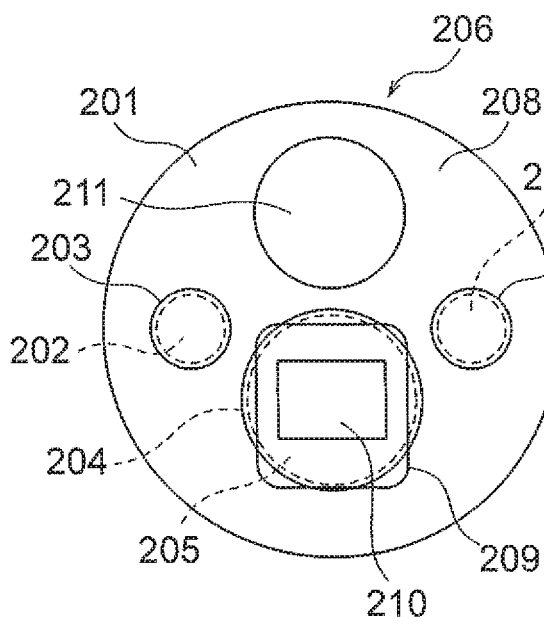
Figure 8C:
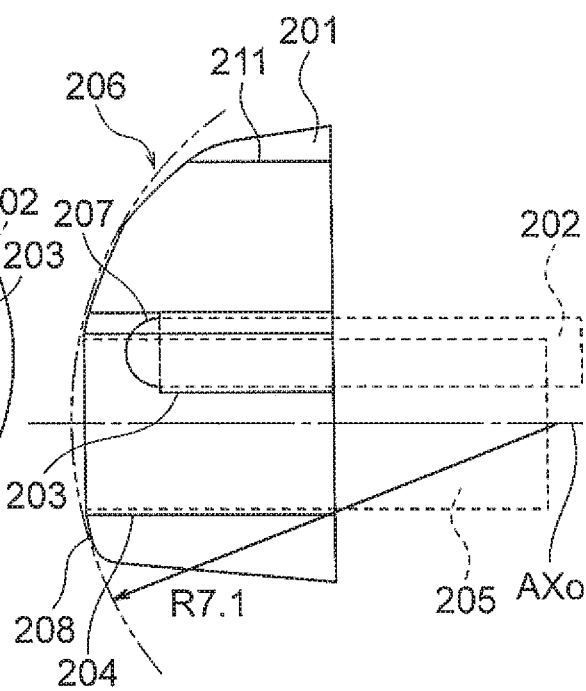
Figure 9A:
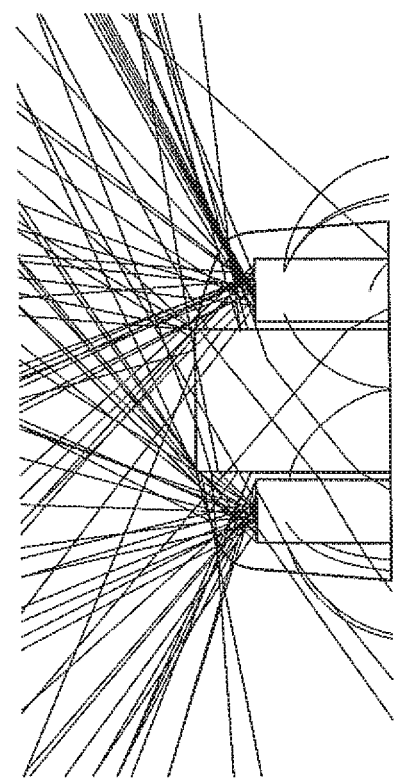
FIG. 9A and FIG. 9B are diagrams showing illumination light in the endoscope illuminating optical system according to the example 2.
Figure 9B:
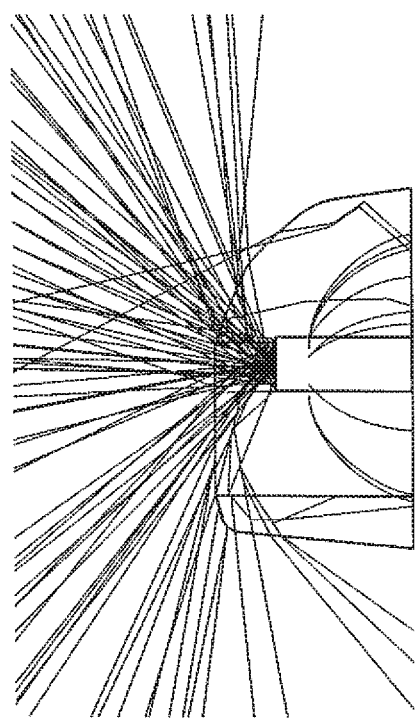
Figure 10:
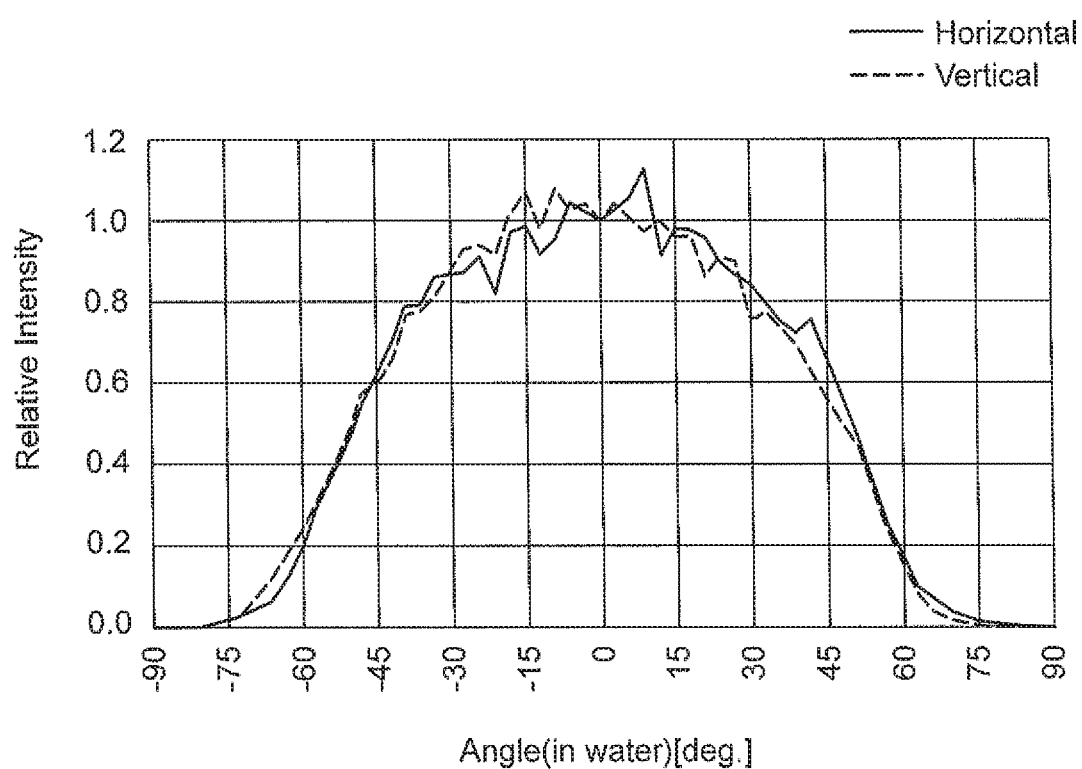
FIG. 10 is a graph showing light distribution characteristics in water of the example 2.

An endoscope illuminating optical system according to the example 2 will be described below. FIG. 8A, FIG. 8B, and FIG. 8C are schematic diagrams showing an arrangement of the endoscope illuminating optical system according to the example 2. FIG. 8A is a top view, FIG. 8B is a front view, and FIG. 8C is a side view. FIG. 9A and FIG. 9B are diagrams showing illumination light in the endoscope illuminating optical system according to the example 2. FIG. 9A is a light-ray diagram showing diffusion of light rays in the horizontal direction, and FIG. 9B is a light-ray diagram showing diffusion of light rays in the vertical direction. FIG. 10 is a graph showing light distribution characteristics in water of the example 2. All these diagrams are made with conditions same as for the example 1.

An endoscope illuminating optical system. 200 is disposed at a front end of an insertion portion of an endoscope. The endoscope illuminating optical system 200 includes a transparent resin member 201 and a lighting member 202.

A non-through hole 203 and a through hole 204 are formed in the transparent resin member 201. The non-through hole 203 is a hole for disposing the lighting member 202. The through hole 204 is a hole for disposing an image pickup member 205.

In the non-through hole 203, the hole does not reach an outer surface 206 of the transparent resin member 201. An internal optical surface 207 is formed at an interior of the transparent resin member 201, at a position opposite to the lighting member 202. A shape of the internal optical surface 207 is concave toward the image side. Moreover, a curved-surface area 208 is positioned on the outer surface 206, at a position opposite to the internal optical surface 207.

The image pickup member 205 includes a solid image pickup element 209 and an objective optical system. In FIG. 8B, an image pickup effective range 210 on an image pickup surface is shown by a rectangular shape. A channel opening 211 is formed inside the transparent resin member 201.

Here, 'R 7.1' in FIG. 8A and FIG. 8C indicates that the curved-surface area 208 is a spherical surface having a radius of curvature 7.1 mm. The spherical surface has a center of curvature on a central axis AXo of the image pickup member 205. A position of the center of curvature of the spherical surface is determined to be such that the spherical surface makes a contact near an outer periphery of the image pickup member 205.

The curved-surface area 208 has a shape which is displaced toward the hand side of the insertion portion, directed from the area near a boundary with the image pickup member 205 toward the outer periphery of the insertion portion, and a shape such that, in the orientation directed toward the internal optical surface 207 from the central axis AXo of the image pickup member 205, the displacement and the angle of inclination increase continuously and monotonously with being directed toward the outer periphery from the central axis AXo of the image pickup member 205.

As shown in FIG. 8A and FIG. 8C, the spherical surface having a radius of curvature 7.1 mm occupies a large portion of a front-end outer surface. However, the radius of curvature of the spherical surface in the example 2 is larger compared to the radius of curvature of the spherical surface in the example 1. Therefore, the curved-surface area 208 is divided into another spherical surface near the periphery on the channel opening 211 side where the illumination light does not reach. By doing so, the outer surface 206 is corrected to be a tapered and smooth surface.

The transparent resin member 201 in the example 2 has a tapering tendency inferior to the tapering tendency of the transparent resin member 101 in the example 1. However, as a tapered shape, the transparent resin member 201 is superior to the transparent resin member 501 in the example for comparison.

According to the light-ray diagrams in FIG. 9A and FIG. 9B, in the example 2, light is diffused almost evenly in both the horizontal direction and the vertical direction, to be directed toward the object space in water. According to the light-distribution graph shown in FIG. 10, there is no shoulder as seen in the light-distribution graph of the example for comparison. Therefore, in the endoscope illuminating optical system according to the example 2, there is no uneven light distribution that may become a tangible damage.

Moreover, when compared with the light-distribution graph in the example for comparison shown in FIG. 19, in the endoscope illuminating optical system according to the example 2, the angle of light distribution not smaller than 45° in the horizontal direction has been secured. Therefore, in this regard, the endoscope illuminating optical system according to the example 2 is superior.

Figure 11A:
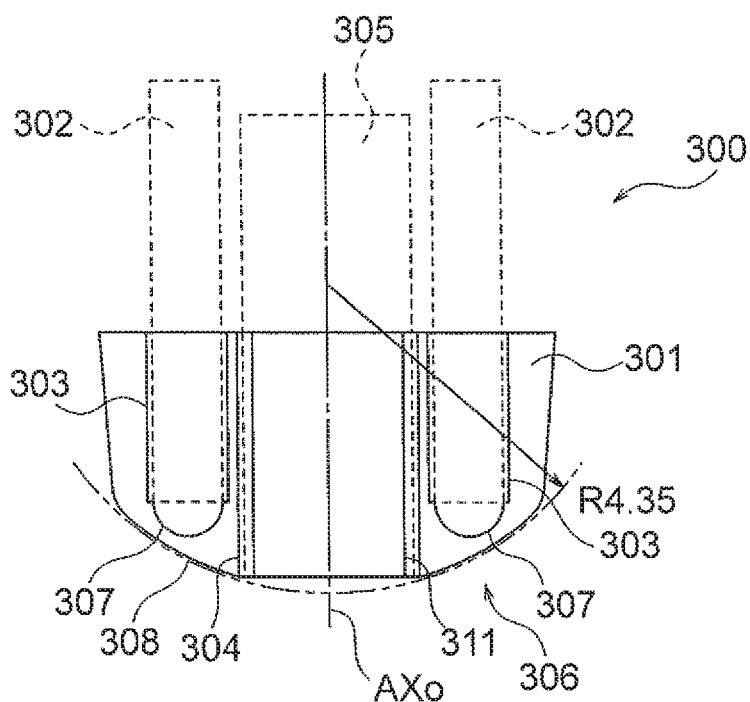
FIG. 11A, FIG. 11B, and FIG. 11C are schematic diagrams showing an arrangement of an endoscope illuminating optical system according to an example 3.
Figures 11B, 11C:
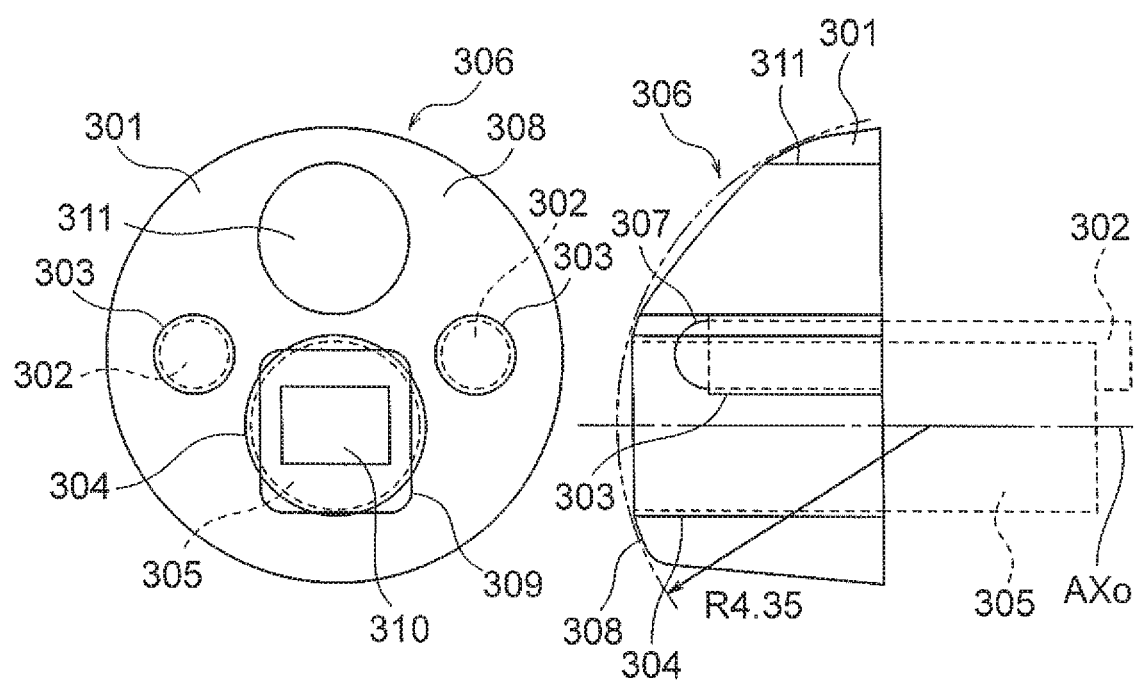
Figure 12A:
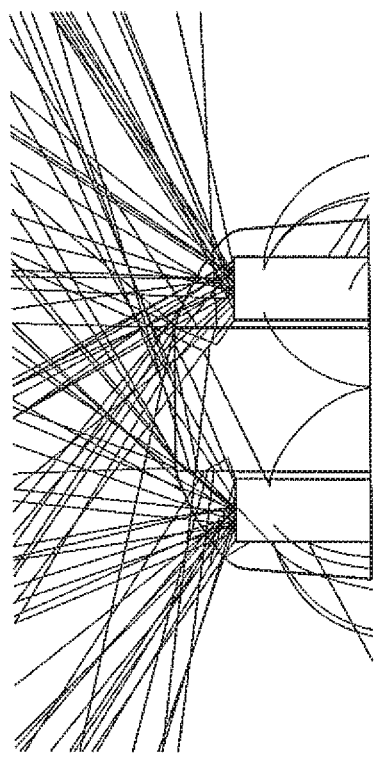
FIG. 12A and FIG. 12B are diagrams showing illumination light in the endoscope illuminating optical system of the example 3.
Figure 12B:
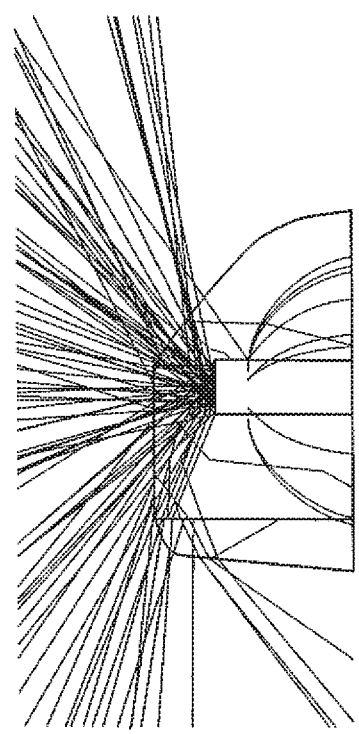
Figure 13:
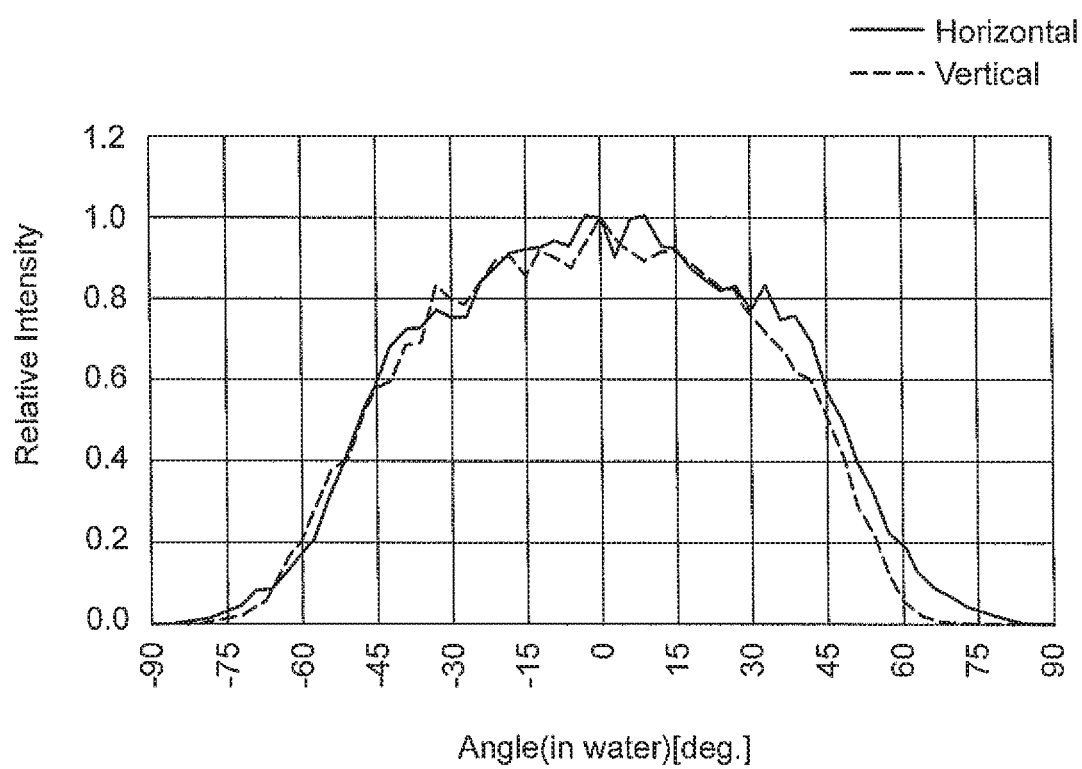
FIG. 13 is a graph showing light distribution characteristics in water of the example 3.

An endoscope illuminating optical system according to the example 3 will be described below. FIG. 11A, FIG. 11B, and FIG. 11C are schematic diagrams showing an arrangement of the endoscope illuminating optical system according to the example 3. FIG. 11A is a top view, FIG. 11B is a front view, and FIG. 11C is a side view. FIG. 12A and FIG. 12B are diagrams showing illumination light in the endoscope illuminating optical system according to the example 3. FIG. 12A is a light-ray diagram showing diffusion of light rays in the horizontal direction, and FIG. 12B is a light-ray diagram showing diffusion of light rays in the vertical direction. FIG. 13 is a graph showing light distribution characteristics in water of the example 3. All these diagrams are made with conditions same as for the other examples.

An endoscope illuminating optical system 300 is disposed at a front end of an insertion portion of an endoscope. The endoscope illuminating optical system 300 includes a transparent resin member 301 and a lighting member 302.

A non-through hole 303 and a through hole 304 are formed in the transparent resin member 301. The non-through hole 303 is a hole for disposing the lighting member 302. The through hole 304 is a hole for disposing an image pickup member 305.

In the non-through hole 303, the hole does not reach an outer surface 306 of the transparent resin member 301. An internal optical surface 307 is formed at an interior of the transparent resin member 301, at a position opposite to the lighting member 302. A shape of the internal optical surface 307 is concave toward the image side. Moreover, a curved-surface area 308 is positioned on an outer surface 306, at a position opposite to the internal optical surface 307.

The image pickup member 305 includes a solid image pickup element 309 and an objective optical system. In FIG. 11B, an image pickup effective range 310 on an image pickup surface is shown by a rectangular shape. A channel opening 311 is formed inside the transparent resin member 301.

Here, 'R 4.35' in FIG. 11A and FIG. 11C indicates that the curved-surface area 308 is a spherical surface having a radius of curvature 4.35 mm. The spherical surface has a center of curvature on a central axis AXo of the image pickup member 305. A position of the center of curvature of the spherical surface is determined to be such that the spherical surface makes a contact near an outer periphery of the image pickup member 305.

The curved-surface area 308 has a shape which is displaced toward the hand side of the insertion portion, directed from the area near a boundary with the image pickup member 305 toward the outer periphery of the insertion portion, and a shape such that, in the orientation directed toward the internal optical surface 307 from the central axis AXo of the image pickup member 305, the displacement and the angle of inclination increase continuously and monotonously with being directed toward the outer periphery from the central axis AXo of the image pickup member 305.

As shown in FIG. 11A and FIG. 11C, the spherical surface having a radius of curvature 4.35 mm occupies a large portion of a front-end outer surface. The radius of curvature of the spherical surface in the example 3 is smaller compared to the radius of curvature of the spherical surface in the example 1. Therefore, the transparent resin member 301 in the example 3 has a shape more tapered and smoother than the shape of the transparent resin member 101 in the example 1. The transparent resin member 301 in the example 3 has a superior insertability.

According to the light-ray diagrams in FIG. 12A and FIG. 12B, in the example 3, light is diffused almost evenly in both the horizontal direction and the vertical direction, to be directed toward the object space in water. According to the light-distribution graph shown in FIG. 13, there is no shoulder as seen in the light-distribution graph of the example for comparison. Therefore, in the endoscope illuminating optical system according to the example 3, there is no uneven light distribution that may become a tangible damage.

Moreover, when compared with the light-distribution graph in the example for comparison shown in FIG. 19, in the endoscope illuminating optical system according to the example 3, the angle of light distribution not smaller than 45° in the horizontal direction has been secured. Therefore, in this regard, the endoscope illuminating optical system according to the example 3 is superior.

Figure 14A:
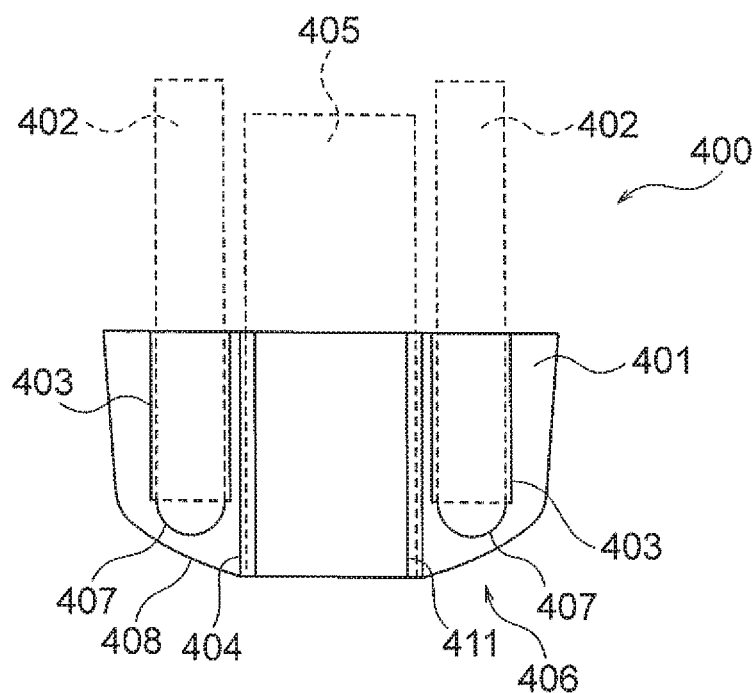
FIG. 14A, FIG. 14B, and FIG. 14C are schematic diagrams of an arrangement of an endoscope illuminating optical system according to an example 4.
Figures 14B, 14C:
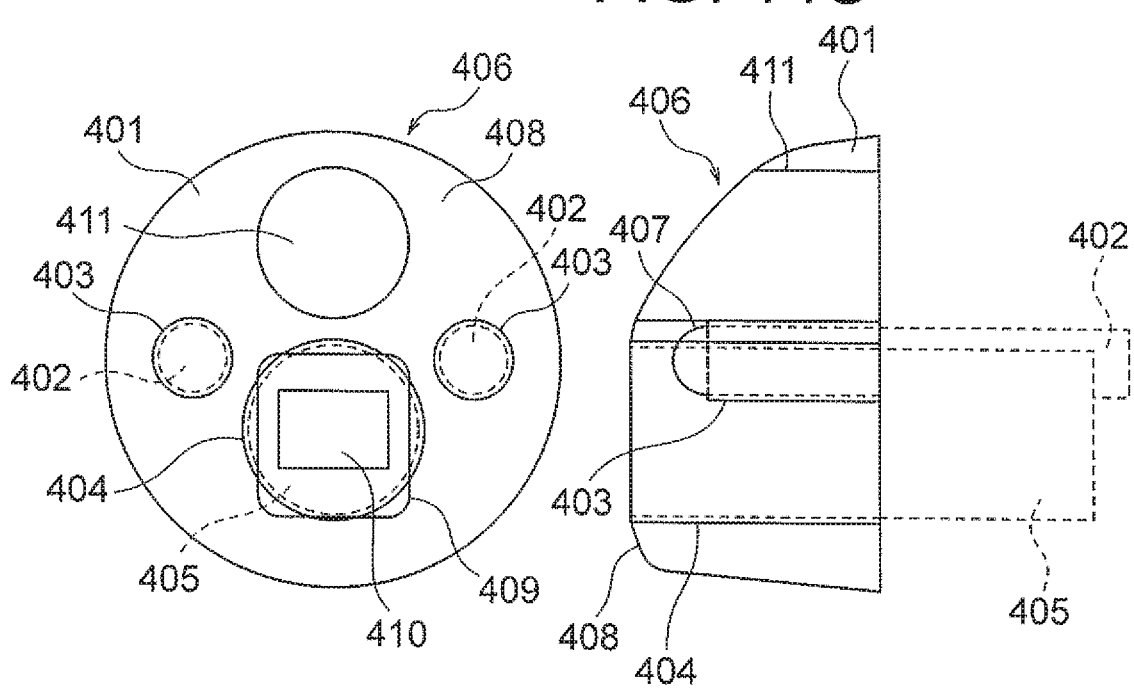
Figure 15A:
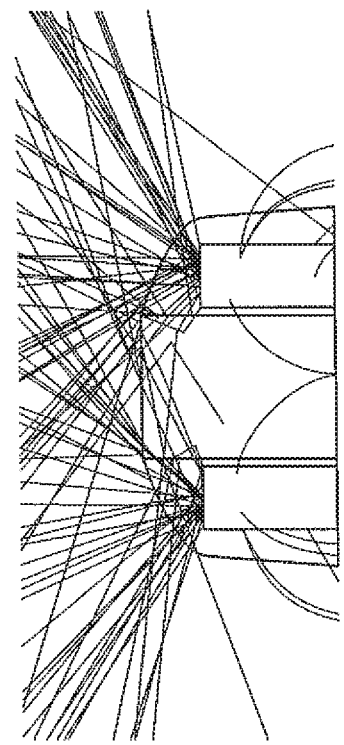
FIG. 15A and FIG. 15B are diagrams showing illumination light in the endoscope illuminating optical system of the example 4.
Figure 15B:
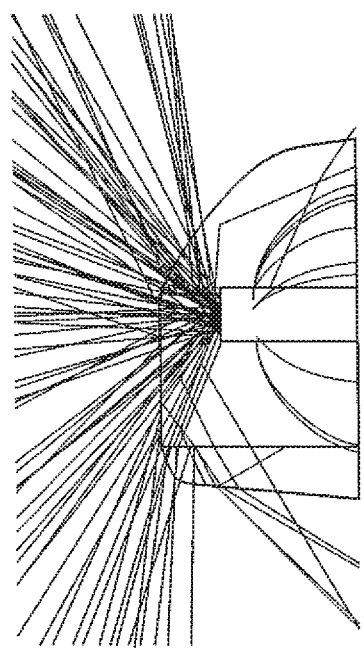
Figure 16:
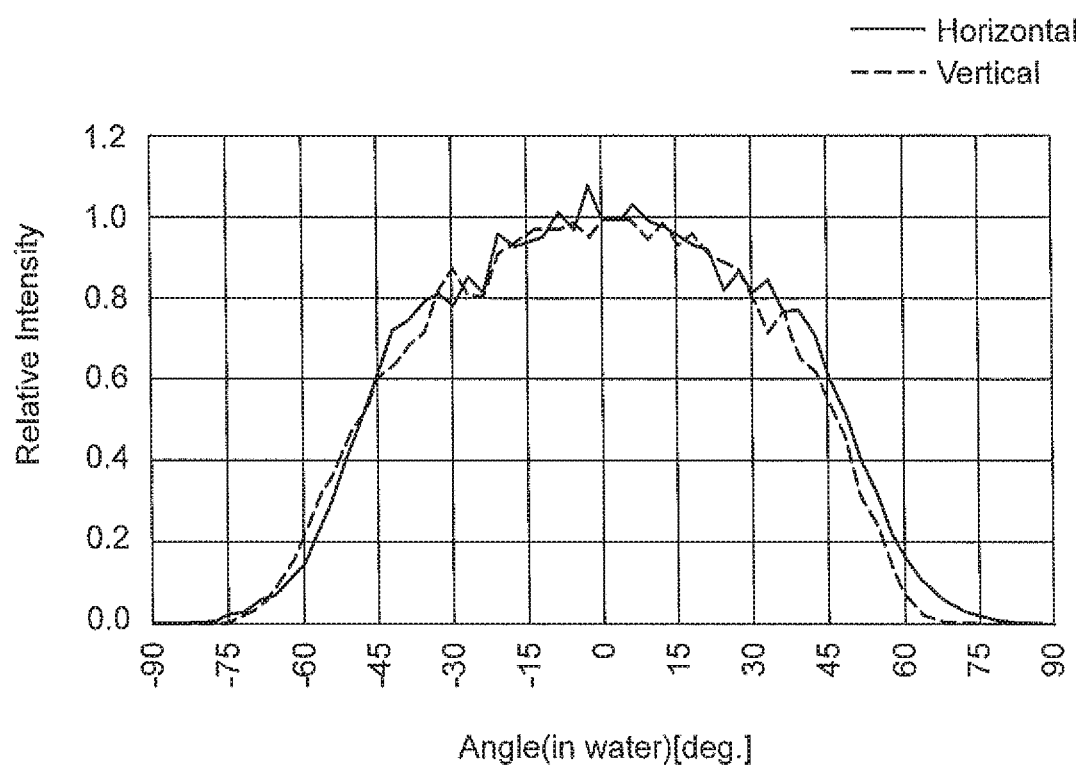
FIG. 16 is a graph showing light distribution characteristics in water of the example 4.

An endoscope illuminating optical system according to the example 4 will be described below. FIG. 14A, FIG. 14B, and FIG. 14C are schematic diagrams showing an arrangement of the endoscope illuminating optical system according to the example 4. FIG. 14A is a top view, FIG. 14B is a front view, and FIG. 14C is a side view. FIG. 15A and FIG. 15B are diagrams showing illumination light in the endoscope illuminating optical system according to the example 4. FIG. 15A is a light-ray diagram showing diffusion of light rays in the horizontal direction, and FIG. 15B is a light-ray diagram showing diffusion of light rays in the vertical direction. FIG. 16 is a graph showing light distribution characteristics in water of the example 4. All these diagrams are made with conditions same as for the other examples.

An endoscope illuminating optical system 400 is positioned at a front end of an insertion portion of an endoscope. The endoscope illuminating optical system 400 includes a transparent resin member 401 and a lighting member 402.

A non-through hole 403 and a through hole 404 are formed in the transparent resin member 401. The non-through hole 403 is a hole for disposing the lighting member 402. The through hole 404 is a hole for disposing an image pickup member 405.

In the non-through hole 403, the hole does not reach an outer surface 406 of the transparent resin member 401. An internal optical surface 407 is formed at an interior of the transparent resin member 401, at a position opposite to the lighting member 402. A shape of the internal optical surface 407 is concave toward the image side. Moreover, a curved-surface area 408 is positioned on an outer surface 406, at a position opposite to the internal optical surface 407.

The image pickup member 405 includes a solid image pickup element 409 and an objective optical system. In FIG. 14B, an image pickup effective range 410 on an image pickup surface is shown by a rectangular shape. A channel opening 411 is formed inside the transparent resin member 401.

In the example 4, the curved-surface area 408 is an axisymmetric aspheric surface. In the parameters of numerical expression (A), it is an aspheric surface defined by R=5.0 mm and K=0.37. A value of K being positive, the curved-surface area 408 has a shape such that the displacement increases to be more than that for a reference surface having a radius of curvature 5.0 mm, with being drawn closer to an outer periphery.

The curved-surface area 408 has a shape which is displaced toward the hand side of the insertion portion, directed from the area near a boundary with the image pickup member 405 toward the outer periphery of the insertion portion, and a shape such that, in the orientation directed toward the internal optical surface 407 from the central axis AXo of the image pickup member 405, the displacement and the angle of inclination increase continuously and monotonously with being directed toward the outer periphery from the central axis AXo of the image pickup member 405.

As shown in FIG. 14A and FIG. 14B, the aspheric surface occupies a large portion of the front-end outer surface. For the aspheric surface in the example 4, the displacement in a direction along the central axis AXo is large as compared to the displacement for the spherical surface in the example 1. Therefore, the transparent resin member 401 in the example 4 has a shape more tapered and smoother than the shape of the transparent resin member 101 in the example 1 having the same radius of curvature at a central portion. The transparent resin member 401 in the example 4 has a superior insertability.

According to the light-ray diagrams in FIG. 15A and FIG. 15B, in the example 4, light is diffused almost evenly in both the horizontal direction and the vertical direction, to be directed toward the object space in water. According to the light-distribution graph shown in FIG. 16, there is no shoulder as seen in the light-distribution graph of the example for comparison. Therefore, in the endoscope illuminating optical system according to the example 4, there is no uneven light distribution that may become a tangible damage.

Moreover, when compared with the light-distribution graph in the example for comparison shown in FIG. 19, in the endoscope illuminating optical system according to the example 4, the angle of light distribution not smaller than 45° in the horizontal direction has been secured. Therefore, in this regard, the endoscope illuminating optical system according to the example 4 is superior.

The light distribution characteristics in the example 4 are almost same as the light distribution characteristics in the examples 1 to 3. Therefore, in the example 4, an improvement in the insertability is realized by making effective use of the degree of freedom of the aspheric surface, without causing a negative optical effect.

As described heretofore, each of the examples 1 to 4 has a different arrangement. However, each of the examples 1 to 4 satisfies conditional expressions (1) and (2). Conditional expressions (1) and (2) are suitable as essential requirements that are independent of a method for defining the shape of the curved-surface area.

Moreover, all the examples satisfy conditional expressions (3) and (4) in which the curved-surface area is defined by an axisymmetric function expression. Conditional expressions (3) and (4) are suitable as requirements at the time of carrying out the optimum design using the axisymmetric function expression.

Furthermore, all the examples satisfy conditional expression (5) for a case of the curved-surface area being defined by a spherical surface or an axisymmetric aspheric surface.

The values of conditional expressions in each example are shown below.

|  | Example 1 | Example 2 | Example 3 | Example 4 |
|---|---|---|---|---|
| (1) Ziax/Ds | 0.053 | 0.036 | 0.062 | 0.054 |
| (2) Aiax (=A [L]) | 26.1° | 18.0° | 30.3° | 27.1° |
| (3) Z [L]/Z [Ds/2] | 0.331 | 0.346 | 0.319 | 0.317 |
| (4) A [L]/A [Ds/2] | 0.643 | 0.661 | 0.627 | 0.602 |
| (5) Roax/Ds | 0.769 | 1.092 | 0.669 | 0.769 |

The values of parameters in each example are shown below.

|  | Example 1 | Example 2 | Example 3 | Example 4 |
|---|---|---|---|---|
| Ziax (=Z [L]) | 0.343 mm | 0.233 mm | 0.404 mm | 0.353 mm |
| Ds | 6.5 mm | 6.5 mm | 6.5 mm | 6.5 mm |
| Aiax (=A [L]) | 26.1° | 18.0° | 30.3° | 27.1° |

-continued

|  | Example 1 | Example 2 | Example 3 | Example 4 |
|---|---|---|---|---|
| Z [Ds/2] | 1.035 mm | 0.672 mm | 1.268 mm | 1.115 mm |
| A [Ds/2] | 40.5° | 27.2° | 48.3° | 45.0° |
| Roax | 5 mm | 7.1 mm | 4.35 mm | 5 mm |

Each example of the present example will be explained below. As mentioned in the description of the example for comparison, each example and the example for comparison have the same arrangement except for the shape of the outer surface of the transparent resin member and the position in the axial direction of the insertion portion of the internal optical surface which depends on the shape of the outer surface of the transparent resin member. Moreover, the shape of the internal optical surface and the light guide being identical, the light distribution characteristics before being refracted at the outer surface are same in each example and example for comparison. The curved-surface area is a spherical surface in examples 1 to 3, and is an axisymmetric aspheric surface in the example 4.

In all the examples, a slightly inner-side range of a field of view (horizontal field of view in water 118.7° and vertical field of view in water)76.3° in the objective optical system is assumed as an illumination range. In all the examples, the design is made such that the following light distribution characteristics are achieved in water. In the light distribution characteristics, an illuminance ratio for an illuminance at the center is used.

Illuminance ratio in direction of 57° in water of a horizontal direction: 20% or more
Illuminance ratio in direction of 36° in water of a vertical direction: 60% or more The light distribution characteristics of each example and the light distribution characteristics of the example for comparison are shown below. For each numerical value, the illuminance ratio is expressed in percentage. The illuminance at the center in the example 1 is let to be 100%. Values in the horizontal direction are values in a direction of angle 57°. Values in the vertical direction are values in a direction of angle 36°.

|  | Example 1 | Example 2 | Example 3 |
|---|---|---|---|
| Center | 100.0 | 99.0 | 108.2 |
| Horizontal direction | 23.9 | 24.7 | 22.7 |
| Vertical direction | 71.0 | 72.0 | 71.7 |

|  | Example 4 | Example for comparison |
|---|---|---|
| Center | 103.5 | 99.4 |
| Horizontal direction | 23.1 | 25.7 |
| Vertical direction | 75.0 | 66.6 |

As shown above, in all the examples, the improved light distribution that has been intended is realized. Moreover, the illuminance ratio at the center is approximately 100% in all the examples. Therefore, even at the center, the illuminance is almost equal in all the examples. In such manner, regarding the efficiency that is sought in an illuminating optical system, there is no large difference in each example. Even in the light distribution characteristics of the example for comparison, with regard to the illuminance ratio at the center, it is almost equal to that in each example. However, as mentioned above, with regard to the unevenness in light distribution, there is a large difference between the example for comparison and each of the example.

With regard to the transparent resin member and the channel opening, the examples and the example for comparison have some common parameters. The common parameters are shown in table 1. An XY coordinate system is defined as follows. A center of the maximum outer diameter of the transparent resin member is let to be a point of origin of XY coordinates. An upward direction in an outer-diameter cross section is let to be a positive side of Y-axis, and a leftward direction in the outer-diameter cross section is let to be a positive side of X-axis. The outer-diameter cross section is a cross section when the transparent resin member is viewed from the object-space side.

TABLE 1

| Transparent resin member |  | Material | Polysulfone resin |
|---|---|---|---|
|  |  | Refractive index for d-line | 1.635 |
|  |  | Maximum outer diameter (Ds) | 6.5 mm |
| Channel opening |  | XY coordinates of central axis | (0 mm, 1.64 mm) |
|  |  | Inner diameter | 2.1 mm |
| Image pickup member |  | XY coordinates of central axis | (0 mm, −1.01 mm) |
|  |  | Maximum outer diameter | 2.55 mm |
| Light guide | Light guide 1 | XY coordinates of central axis | (−1.95 mm, 0 mm) |
|  | Light guide 2 | XY coordinates of central axis | (1.95 mm, 0 mm) |
|  | Common for light guides 1 and 2 | Shape of light emitting surface | Circular |
|  |  | Outer diameter of light emitting surface | 1 mm |
| Internal optical surface | Internal optical surface 1 | XY coordinates of central axis | (−1.95 mm, 0 mm) |
|  | Internal optical surface 2 | XY coordinates of central axis | (1.95 mm, 0 mm) |
|  | Common for internal optical surfaces 1 and 2 | Outer peripheral shape | Circular |
|  |  | Effective diameter | 1.06 mm |
|  |  | Depth of concave surface | 0.5 mm |
|  |  | Shape of concave surface | Aspheric |
|  |  | Value of parameter | R = 0.456<br>K = −0.3 |
|  |  | Thickness of concave surface portion* | 0.25 mm |

*a distance between the concave surface and outer surface on the central axis of the light guide.

For each of the examples and the example for comparison, specifications related to the optically effective range of the transparent resin member are shown in table 2. Here, R denotes the radius of curvature and K denotes a coefficient which determines the quadratic surface characteristics. Moreover, $\theta$ denotes the angle of inclination. The inclination generates toward a center of an image pickup portion. Furthermore, $\Phi$ denotes a diameter, YU denotes an upper end, YL denotes a lower end, XL denotes a left end, and XR denotes a right end.

The example of comparison has two optically effective ranges. The two optically effective ranges are provided symmetrically. An outer-diameter dimension is a dimension in one of the optically effective ranges. Moreover, X1 denotes an end on the image pickup side, and XR denotes an end on the outer-periphery side.

TABLE 2

| | Type | Optically effective range of transparent resin member | | | |
|---|---|---|---|---|---|
| | | Surface shape | Shape dimension | Outer peripheral shape | Outer peripheral dimension |
| Example 1 | Curved-surface area | Spherical | R = 5.0 mm | Substantially circular | Φ = 5.9 mm |
| Example 2 | Curved-surface area | Spherical | R = 7.1 mm | | YU = 1.88 mm<br>YL = −2.74 mm<br>XL = −2.88 mm<br>XR = 2.88 mm |
| Example 3 | Curved-surface area | Spherical | R = 4.35 mm | Substantially circular | Φ = 6.12 mm |
| Example 4 | Curved-surface area | Aspheric | R = 5.0 mm<br>K = 0.37 | Substantially circular | Φ = 6.12 mm |
| Example for comparison | Inclined flat surface portion | Flat | θ = 15° | | YU = 1.15 mm<br>YL = −1.85 mm<br>X1 = 1.16 mm<br>X2 = 2.91 mm |

Figure 22A:
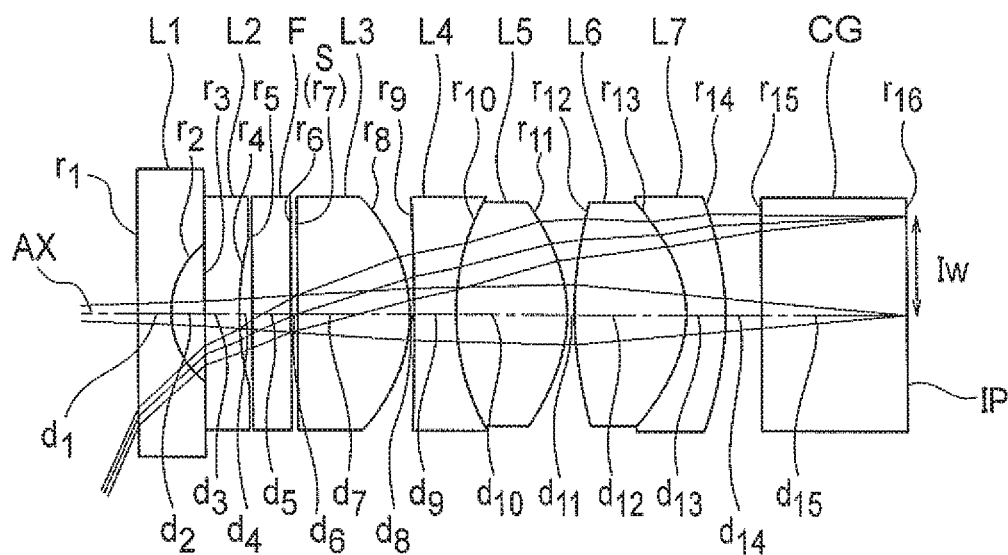
FIG. 22A and FIG. 22B are diagrams showing an optical path and a lens cross-sectional view of an objective optical system.
Figure 22B:
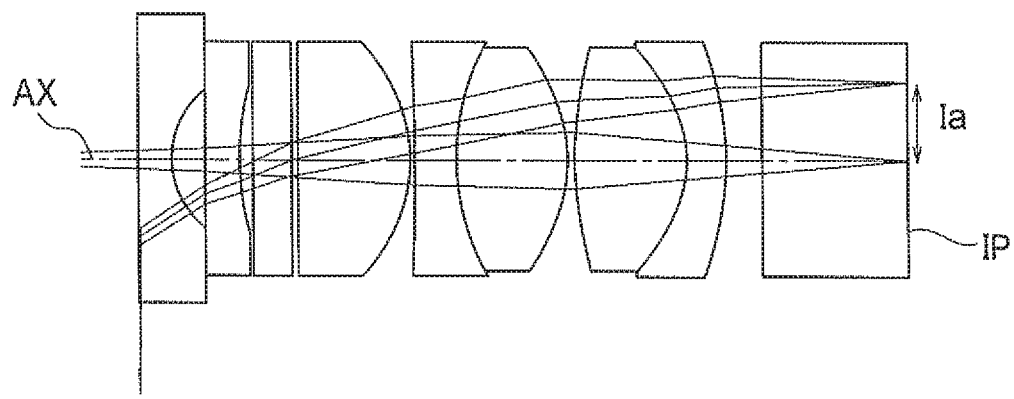

An example of the objective optical system will be described below. The objective optical system is used for the image pickup member in the examples 1 to 4. FIG. 22A and FIG. 22B are diagrams showing a lens cross-sectional view and an optical path of the objective optical system. FIG. 22A shows a lens cross-sectional view and an optical path in water of the objective optical system. FIG. 22B shows a lens cross-sectional view and an optical path in air of the objective optical system.

The objective optical system includes in order from an object side, a planoconcave negative lens L1 of which an object side is a flat surface, a planoconcave negative lens L2 of which an object side is a flat surface, a plane parallel plate F, a planoconvex positive lens L3 of which an object side is a flat surface, a biconcave negative lens L4, a biconvex positive lens L5, a biconvex positive lens L6, a negative meniscus lens L7, and a cover glass CG. Here, the biconcave negative lens L4 and the biconvex positive lens L5 are cemented. The biconvex positive lens L6 and the negative meniscus lens L7 are cemented. AX denotes an optical axis.

An aperture stop S is disposed on an object-side surface of the planoconvex positive lens L3.

Numerical data of the objective optical system is shown below. In symbols, r denotes radius of curvature of each lens surface, d denotes a distance between respective lens surfaces, nd denotes a refractive index of each lens for a d-line, Vd denotes an Abbe number for each lens, FNO denotes an F number, moreover, focal length is a focal length for a d-line. STO denotes an aperture stop, IP denotes an image plane.

EXAMPLE 1

Unit mm

Surface data

| Surface no. | r | d | nd | vd |
|---|---|---|---|---|
| 1 | ∞ | 0.25 | 1.76820 | 71.79 |
| 2 | 0.639 | 0.27 | | |
| 3 | ∞ | 0.25 | 2.00330 | 28.27 |

-continued

Unit mm

| | | | | |
|---|---|---|---|---|
| 4 | 1.961 | 0.11 | | |
| 5 | ∞ | 0.30 | 1.52134 | 74.98 |
| 6 | ∞ | 0.03 | | |
| 7 | ∞ (STO) | 0.87 | 2.00330 | 28.27 |
| 8 | −1.243 | 0.05 | | |
| 9 | −9.813 | 0.30 | 2.00330 | 28.27 |
| 10 | 1.717 | 0.86 | 1.72916 | 54.68 |
| 11 | −1.345 | 0.05 | | |
| 12 | 2.838 | 0.87 | 1.48749 | 70.23 |
| 13 | −1.108 | 0.30 | 1.92286 | 18.90 |
| 14 | −2.439 | 0.28 | | |
| 15 | ∞ | 1.10 | 1.51633 | 64.14 |
| 16 | ∞ (IP) | | | |

Various data

| | |
|---|---|
| focal length (mm) | 0.56 |
| Fno. | 4.153 |
| object distance in water (mm) | 9 |
| maximum lens outer diameter (mm) | 2.2 | image height and field of view at a time of in-water observation

| | IH (mm) | Angle (°) |
|---|---|---|
| diagonal | 0.751 | 129.4 |
| horizontal | 0.706 | 118.7 |
| vertical | 0.482 | 76.3 |

Moreover, Iw in FIG. 22A denotes the maximum image height in a diagonal direction in the in-water observation state. Here, a value of Iw is 0.751 mm. This image height is assumed to be matched with an effective image pickup area of a solid image pickup element. By setting such image height, the entire effective image pickup area of the solid image pickup element is used in the in-water observation state. The in-water field of view in this case is 129.4°, which is an extremely wide angle for the in-water observation, and it is possible to observe an object in water by using the entire effective image pickup area of the solid image pickup element.

Whereas, Ia in FIG. 22B denotes an image height equivalent to the maximum image height in air. A lens surface positioned nearest to an object of the objective optical system being a flat surface, only light rays having the field of view in air of up to 180° can be incident on the lens. A principal light ray which is incident almost parallel to a flat surface positioned nearest to the object reaches a position lower than Iw on an image plane. Therefore, a value of Ia which is equivalent to the maximum image height in air becomes 0.5995 mm. Accordingly, an image in the in-air observation state becomes an image in which the effective image pickup area of the solid image pickup element is used partially, and there is no problem with regard to the practical use in an endoscope intended for observation in air.

Figure 23A:
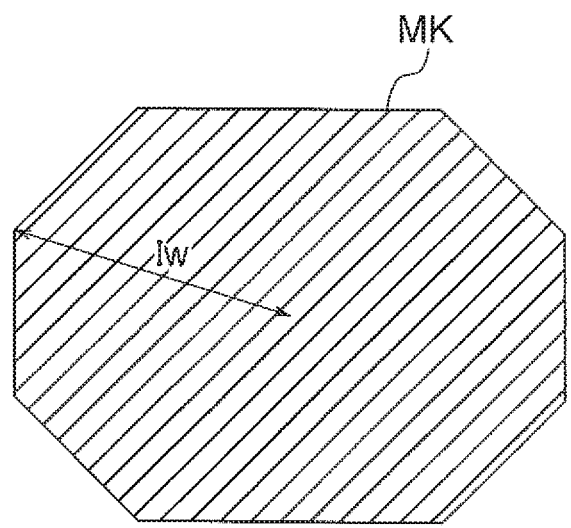
FIG. 23A and FIG. 23B are diagrams showing an image pickup range.
Figure 23B:
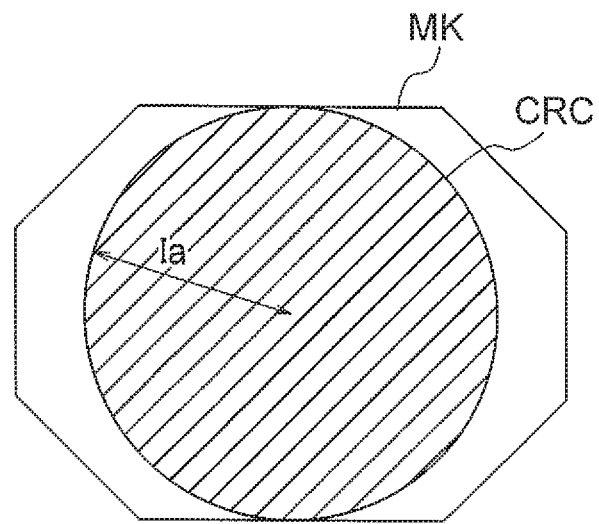

FIG. 23A, and FIG. 23B are diagrams showing an image pickup range. FIG. 23A is a diagram showing an image pickup range at the time of in-water observation. FIG. 23B is a diagram showing an image pickup range at the time of observation in air. FIG. 23A and FIG. 23B are diagrams showing that the effective image pickup area in the in-air observation state becomes narrower than the effective image pickup area in the in-water observation state as described above.

FIG. 23A shows an image pickup area on the solid image pickup element in the in-water observation state. The diagram indicates that by using an octagonal electrical field mask, it is possible to use practically the entire effective image pickup area in an octagonal mask MK shown by hatched lines. The maximum image height in the octagonal mask MK is Iw.

FIG. 23B shows an image pickup area on the solid image pickup element in the in-air observation state. A circle CRC having a radius Ia shown by hatched lines becomes the image pickup area in the in-air observation state, and an area with no hatched lines between the octagonal mask MK and the circle CRC becomes an optically ineffective area in which no object image is formed.

According to such objective optical system, a wide-angle observation is possible even in the in-water state when the surface nearest to the object is a flat surface. Furthermore, when the object side is a flat surface, no special arrangement is required in order to cope with a flare which is caused due to light from an illuminating optical system being incident directly, and there are no unnecessary restrictions on the arrangement of the illuminating optical system. Therefore it is preferable that the object side be a flat surface.

A lens having the maximum lens outer diameter in the objective optical system is a lens at an object side end. The maximum lens outer diameter of this lens is 2.2 mm. In an endoscope for urinary bladder, a channel having an inner diameter of 2.2 mm becomes necessary. When the lens outer diameter is 2.2 mm, even when combined with a channel and a bending mechanism, it is possible to realize an endoscope for urinary bladder with a front-end portion having an outer diameter ($\phi$) less than 7 mm.

It is possible to use the abovementioned objective optical system in the endoscope illuminating optical system of the example 1. The endoscope illuminating optical system of the example 1 satisfies conditional expressions (1) and (2). When a value of Aiax is 35° which is an upper limit value, or more than 35°, the maximum angle of a light ray that can be emerged in the object space in the direction of the image pickup member from that position, made with the central axis of the image pickup member is 55°. In the abovementioned objective optical system, the maximum half field of view in water in the horizontal direction is 59.4°. Therefore, illumination light with the maximum angle 55° is irradiated to an inner side of a field of view near a horizontal end of the objective optical system.

When a right-side end of the field of view is taken as an example, illumination light emerged from an internal optical surface on a right side reaches the right-side end of the field of view without any problem. Whereas, illumination light emerged from an internal optical surface on a left side does not reach the right-side end of the field of view. In this case, a boundary of illuminance is formed at a slightly inner side of the right-side end of the field of view. The illuminance changes at this boundary. This change is visible as uneven light distribution.

Sometimes, a boundary portion may be developed due to overlapping of an illumination area by illumination from the left side and an illumination area by illumination from the right side. When an object distance is short, this boundary portion is in the horizontal field of view in many cases. The boundary portion is determined by factors such as an angle of light rays in illumination light directed toward the illumination area (hereinafter, referred to as 'angle characteristics'), a position of the lighting member, and a position of the image pickup member. However, in a case in which the boundary portion is determined only by the angle characteristics, it is not desirable as it is visible as uneven light distribution at each and every object distance.

The example 1 has two combinations of the internal optical surface and the lighting member. In the example 1, these are disposed to be bilaterally symmetric. However, when there is only one combination of the internal optical surface and the lighting member, the illumination light cannot simply reach a specific portion of image. Therefore, it can be said to be preferable to carry out illumination with a plurality of combinations rather than carrying out the illumination with only one combination.

According to each example, it is possible to provide an endoscope illuminating optical system which is capable of realizing an improvement in the insertability and a reduction of the uneven light distribution.

When an outer diameter of the insertion portion becomes thin, a distance between the lighting member and the image pickup member becomes short. In a case in which the insertion portion is provided with a channel opening, the distance between the lighting member and the image pickup member becomes even shorter. Moreover, when an angle of light distribution is widened in accordance with widening of a field of view of in-water observation, the illumination light passes in the vicinity of the image pickup member and in the vicinity of the channel opening.

In the endoscope illuminating optical system according to the present embodiment, a large area of the outer surface is occupied by the curved-surface area. Therefore, even in a case in which the outer diameter of the insertion portion has become thin or a case in which the angle of light distribution has become wide, it is possible to realize a reduction of uneven light distribution while securing an improved insertability. As a result, it is possible to mount the endoscope illuminating optical system easily on a thin-diameter endoscope with a wide angle.

The present embodiment shows an effect that is possible to provide an endoscope illuminating optical system which is capable of realizing an improvement in the insertability and a reduction of the uneven light distribution.

As described heretofore, the present invention is useful for an endoscope illuminating optical system which is capable of realizing an improvement in the insertability and a reduction of the uneven light distribution.

What is claimed is:

1. An endoscope illuminating optical system, comprising:
   a transparent resin member; and
   a lighting member which outputs illumination light, wherein:
the transparent resin member has:
- a through hole in which an image sensor is disposed,
- a non-through hole in which the lighting member is disposed,
- an internal optical surface which is formed at an interior of the transparent resin member by the non-through hole, and
- an outer surface from which the illumination light incident on the transparent resin member via the internal optical surface emerges toward an object, the outer surface has a curved-surface area through which the illumination light passes,
the curved-surface area has a boundary with the through hole,
in the curved-surface area, a displacement of each point of the curved-surface area from the boundary occurs in a direction away from the object,
a shape of the curved-surface area in a cross section defined by a plane including a central axis of the through hole is a shape such that an angle of inclination at each point in the curved-surface area increases in accordance with an increase in distance away from the central axis, and
the following conditional expressions (1) and (2) are satisfied:

$$0.02 < Ziax/Ds < 0.08 \quad (1), \text{ and}$$

$$10° < Aiax < 35° \quad (2)$$

where,
Ziax denotes a distance from a predetermined position to the boundary, as measured along the central axis, and here
the predetermined position is a position at which an axis, which passes through a center of gravity of the internal optical surface and is parallel to the central axis, intersects the curved-surface area, and
regarding the sign, either positive or negative, of the distance, the distance is let to be positive when the boundary is positioned on an object side of the predetermined position,
Ds denotes a maximum outer diameter of the transparent resin member, and
Aiax denotes an angle of inclination at the predetermined position for a cross-sectional shape of the curved-surface area in a cross-section defined by a plane including the central axis and the predetermined position, and here
the angle of inclination is an angle made by a tangent to the cross-sectional shape and an axis perpendicular to the central axis.

2. The endoscope illuminating optical system according to claim 1, wherein:
- a plurality of the non-through holes are provided,
- a plurality of the lighting members are provided,
- each of the plurality of lighting members is disposed in a respective one of the plurality of non-through holes, and
- at least two non-through holes from among the plurality of non-through holes are formed to be mirror-symmetric with respect to at least one of the cross-sections defined by a plane including the central axis.

3. The endoscope illuminating optical system according to claim 1, wherein:
the shape of the curved-surface area is axisymmetric having an axis of symmetry near the central axis, and is definable by a function expression in which a distance from the axis of symmetry is let to be a variable, and
the following conditional expressions (3) and (4) are satisfied:

$$0.15 < Z[L]/Z[Ds/2] < 0.55 \quad (3), \text{ and}$$

$$0.4 < A[L]/A[Ds/2] < 0.8 \quad (4)$$

where,
Z [r] denotes a function expressing a displacement at a point on the curved-surface area, separated away only by a distance r from the axis of symmetry, and here the displacement is a distance from a point on the curved-surface area to the boundary, as measured along the central axis,
A [r] denotes a function expressing an angle of inclination based on a differential coefficient of Z [r] at the point on the curved-surface area, separated apart only by the distance r from the axis of symmetry, and
L denotes a distance from the axis of symmetry to the center of gravity of the internal optical surface.

4. The endoscope illuminating optical system according to claim 1, wherein:
the curved-surface area is one of a spherical surface and an aspheric surface having an axis of symmetry near the central axis, and
the following conditional expression (5) is satisfied:

$$0.55 < Roax/Ds < 2 \quad (5)$$

where,
Roax denotes an absolute value of a radius of curvature at a central portion of the one of the spherical surface and the aspheric surface.

5. The endoscope illuminating optical system according to claim 1, wherein the lighting member comprises one of a light guide and a light emitter.

* * * * *